(12) United States Patent
Porges

(10) Patent No.: US 10,702,154 B2
(45) Date of Patent: Jul. 7, 2020

(54) SYSTEMS AND METHODS FOR MODULATING PHYSIOLOGICAL STATE

(71) Applicant: Polyvagal Science LLC, Chapel Hill, NC (US)

(72) Inventor: Stephen Porges, Bloomington, IN (US)

(73) Assignee: Polyvagal Science LLC, Atlantic Beach, FL (US)

( * ) Notice: Subject to any disclaimer, the term of this patent is extended or adjusted under 35 U.S.C. 154(b) by 0 days.

(21) Appl. No.: 16/289,802

(22) Filed: Mar. 1, 2019

(65) Prior Publication Data

US 2019/0269328 A1 Sep. 5, 2019

Related U.S. Application Data

(60) Provisional application No. 62/637,251, filed on Mar. 1, 2018.

(51) Int. Cl.
*A61B 5/00* (2006.01)
*A61B 5/04* (2006.01)
(Continued)

(52) U.S. Cl.
CPC .............. *A61B 5/0006* (2013.01); *A61B 5/01* (2013.01); *A61B 5/02007* (2013.01); *A61B 5/02405* (2013.01); *A61B 5/02416* (2013.01); *A61B 5/0402* (2013.01); *A61B 5/04005* (2013.01); *A61B 5/0496* (2013.01);
(Continued)

(58) Field of Classification Search
CPC . A61B 5/0006; A61B 5/04005; A61B 5/0402; A61B 5/0496; A61B 5/14539; A61B 5/02007; A61B 5/1455; A61B 5/02405; A61B 5/01; A61B 5/02416
See application file for complete search history.

(56) References Cited

U.S. PATENT DOCUMENTS 3,757,769 A 9/1973 Arguimbau et al.
3,949,735 A 4/1976 Klar et al.
(Continued)

FOREIGN PATENT DOCUMENTS

EP 0674874 A2 10/1995

OTHER PUBLICATIONS

International Search Report and Written Opinion issued for PCT/US2019/020202, dated Jul. 1, 2019, 9 pp.
(Continued)

*Primary Examiner* — Eric F Winakur
(74) *Attorney, Agent, or Firm* — Zeller IP Group, PLLC; Kyle M. Zeller

(57) ABSTRACT

Methods and systems are provided to monitor bio-signals associated with one or more physiological structures of a subject, process the bio-signals to determine neural information, determine a current state of the subject based on the neural information, determine feedback to be provided to the subject based on the current neural state and a desired neural state, and/or to provide the feedback to the subject in order to modify the subject's current neural state to the desired neural state. The neural information may include validated neural indices relating to dynamic regulation of the monitored physiological structures via identifiable neural pathways and/or neural metrics quantified from such neural indices.

37 Claims, 8 Drawing Sheets

(51) Int. Cl.
| | |
|---|---|
| *A61B 5/0402* | (2006.01) |
| *G06N 3/02* | (2006.01) |
| *A61B 5/0496* | (2006.01) |
| *A61B 5/024* | (2006.01) |
| *A61B 5/1455* | (2006.01) |
| *A61B 5/01* | (2006.01) |
| *G16H 10/60* | (2018.01) |
| *A61B 5/02* | (2006.01) |
| *A61B 5/0476* | (2006.01) |
| *A61B 5/145* | (2006.01) |
| *A61B 5/053* | (2006.01) |

(52) U.S. Cl.
CPC ............ *A61B 5/1455* (2013.01); *G06N 3/02* (2013.01); *G16H 10/60* (2018.01); *A61B 5/0476* (2013.01); *A61B 5/0533* (2013.01); *A61B 5/14539* (2013.01); *A61B 5/486* (2013.01); *A61B 2576/023* (2013.01)

(56) References Cited

U.S. PATENT DOCUMENTS

| | | | |
|---|---|---|---|
| 4,510,944 | A | 4/1985 | Porges |
| 5,699,809 | A | 12/1997 | Combs et al. |
| 5,792,072 | A | 8/1998 | Keefe |
| 5,868,682 | A | 2/1999 | Combs et al. |
| 5,954,669 | A | 9/1999 | Iseberg |
| 6,048,320 | A | 4/2000 | Edward |
| 6,986,747 | B2* | 1/2006 | McCulloch ........... A61B 5/1455 600/26 |
| 7,231,240 | B2* | 6/2007 | Eda ..................... A61B 5/14553 600/322 |
| 8,737,631 | B2 | 5/2014 | Boretzki et al. |
| 9,333,372 | B2 | 5/2016 | Otis |
| 10,029,068 | B2 | 7/2018 | Porges |
| 10,426,956 | B2 | 10/2019 | Williamson et al. |
| 2005/0131272 | A1 | 6/2005 | Waldmann |
| 2006/0101935 | A1 | 5/2006 | Nakatani et al. |
| 2006/0122675 | A1 | 6/2006 | Libbus et al. |
| 2006/0122676 | A1 | 6/2006 | Ko et al. |
| 2008/0147138 | A1 | 6/2008 | Maskara et al. |
| 2008/0194984 | A1 | 8/2008 | Keefe |
| 2008/0249439 | A1 | 10/2008 | Tracey et al. |
| 2008/0319513 | A1 | 12/2008 | Pu et al. |
| 2009/0187230 | A1 | 7/2009 | DiLorenzo |
| 2009/0208044 | A1 | 8/2009 | Neher |
| 2009/0234406 | A1 | 9/2009 | Shuros et al. |
| 2010/0016755 | A1 | 1/2010 | Henry et al. |
| 2010/0202645 | A1 | 8/2010 | Puria et al. |
| 2010/0280307 | A1 | 11/2010 | Lineaweaver et al. |
| 2013/0009993 | A1* | 1/2013 | Horseman ............ G16H 40/63 345/633 |
| 2013/0060159 | A1 | 3/2013 | Bromwich et al. |
| 2013/0066395 | A1 | 3/2013 | Simon et al. |
| 2013/0203027 | A1 | 8/2013 | Villers-Sidani et al. |
| 2013/0211471 | A1 | 8/2013 | Libbus et al. |
| 2013/0245722 | A1 | 9/2013 | Ternes et al. |
| 2013/0303941 | A1 | 11/2013 | Porges et al. |
| 2014/0358193 | A1 | 12/2014 | Lyons et al. |
| 2015/0264492 | A1 | 9/2015 | Laudanski et al. |
| 2015/0306395 | A1 | 10/2015 | Libbus et al. |
| 2016/0066847 | A1* | 3/2016 | Sales .................... A61B 5/1176 600/324 |
| 2016/0317041 | A1 | 11/2016 | Porges et al. |
| 2016/0354543 | A1 | 12/2016 | Cinar et al. |

OTHER PUBLICATIONS

Abrams, Daniel et al., Auditory Brainstem Timing Predicts Cerebral Asymmetry for Speech, The Journal of Neuroscience, Oct. 25, 2006, 26(43):11131-11137.
Abrams, Daniel et al., Right-hemisphere auditory cortex is dominant for coding syllable patterns in speech, The Journal of Neuroscience, Apr. 29, 2008, 3958-3965, vol. 28(15).
Ahonniska, Janna et al., Speech perception and brain laterality: the effect of ear advantage on auditory event-related potentials, Brain and Language, 1993, pp. 127-146, 45.
Aibara, Ryuichi et al., Human middle-ear sound transfer function and cochlear input impedance, Hearing Research, 2001, pp. 100-109, 152.
Allen, Jont B. et. al., Evaluation of human middle ear function via an acoustic power assessment, Journal of Rehabilitation Research and Development, 2005, pp. 63-78, 42.
Bachevalier, Jocelyne et al., The orbitofrontal-amygdala circuit and self-Regulation of social-emotional behavior in autism, Neuroscience & Biobehavioral Reviews, 2006, pp. 97-117, 30.
Baguley, David M, Hyperacusis, Journal of the Royal Society of Medicine, 2003, pp. 582-585, 96:12.
Beers, Alison et al., Wideband reflectance in normal caucasian and chinese school-aged children and in children with otitis media with effusion, Ear and Hearing, 2010, pp. 221-233, 31(2), Lippincott Williams & Wilkins, USA.
Boger, Marlene E. et. al., The noise spectrum influence on noise-induced hearing loss prevalence in workers, Brazilian Journal of Otorhinolaryngology, 2009, 328-334, 75(3).
Borg et. al., The middle-ear muscles, Scientific American, 1989, pp. 74-80, 261(2).
Borg, E. On the change in the acoustic impedance of the ear as a measure of middle ear muscle reflex activity, Acta Oto-laryngologica, 1972, pp. 163-171, 74.
Borg, Erik et. al., The activity of the stapedius muscle in man during vocalization, Acta Oto-laryngologica, 1975, pp. 325-333, 79.
Borg, Erik. On the neuronal organization of the acoustic middle ear reflex. A physiological and anatomical study, Brain Research, 1973, pp. 101-123, 49.
Brown, M.C. & Levine, J.L., Dendrites of medial olivocochlear neurons in mouse, Neuroscience, 2008, pp. 147-159, 154(1).
Brown, William, Some experimental results in the correlation of mental abilities, British Journal of Psychology, 1910, pp. 296-322, 3.
Burke, Kenneth S. et. al., On the Zwislocki acoustic bridge, The Journal of the Acoustical Society of America, 1967, 1364, 41.
Colleti, V. et. al., Multifrequency tympanometry, Audiology, 1977, 106-119, 15.
Colleti, V., Tympanometry from 200 to 2000 Hz probe tone, 1976, Audiology, pp. 106-119, 15.
Culling, John F. et. al., Perceptual separation of simultaneous vowels: within and across-formant grouping by f0, The Journal of the Acoustical Society of America, 1993, pp. 3454-3467, 93(6), Acoustical Society of America.
Davila, Maria I., Lewis, Gregory F., & Porges, Stephen W., The Physiocam: a novel non-contact sensor to measure heart rate variability in clinical and field applications, Frontiers in Public Health, 2017, pp. 1-14, 5, Frontiers in Public Health.
Davila, Maria I., Lewis, Gregory F., & Porges, Stephen W., The physiocam: Cardiac pulse, continuously monitored by a color video camera, Journal of Medical Devices, 2016, 10.
Decraemer, Willem et. al., Malleus vibration mode changes with frequency, Hearing Research, 1991, pp. 305-318, 54.
Denver, John et al., Methodological issues in the quantification of respiratory sinus arrhythmia, Biological Psychology, Oct. 25 2006, 286-294, Elsevier B.V.
Dissanayake, Cheryl et al. "Attachment and emotional responsiveness in children with autism, in International Review of Research in Mental Retardation." Academic Press 23 (2000): 239-266.
Erickson, Donna, Articulation of extreme formant patterns for emphasized vowels, Phonetica, 2002, pp. 134-149, 59.
Feeney, M. Patrick et. al., Age effects in the human middle ear: wideband acoustical measures, The Journal of the Acoustical Society of America, 2004, pp. 3546-3558, 116.
Fletcher, Harvey et. al., Loudness, its definition, measurement and calculation, The Journal of the Acoustical Society of America, 1933, pp. 82-108, 5.
Gordon, A.G., Abnormal middle ear muscle reflexes and audiosensitivity, British Journal of Audiology, 1986, pp. 95-99, 20.
Hanks W. D. et al., Middle ear resonance and acoustic immittance measures in children, J. Speech Hear Res. (1993) 36:218-22.

(56) References Cited

OTHER PUBLICATIONS

Hayes, R.W. et. al., Auditory abnormalities in autistic children, The Lancet, 1977, p. 767, 2.
Heffner, Henry E. et. al., Effect of bilateral auditory cortex lesions on absolute thresholds in Japanese macaques, Journal of Neurophysiology, 1990, pp. 191-205, 64.
Homma, Kenji, Shimizu, Yoshitaka, & Puria, Sunil, Ossicular resonance modes of the human middle ear for bone and air conduction, The Journal of the Acoustical Society of America, 2009, pp. 968-979, 125.
Honjo, Iwao et. al., Role of the tensor tympani muscle in eustachian tube function, Acta Otolaryngol., 1983, pp. 329-332, 95.
Hornickel, Jane et. al., Subcortical laterality of speech encoding, Audiology and Neurotology, 2009, pp. 198-207, 14.
Hugdahl et. al., Age effects in dichotic listening to consonant-vowel syllables: interactions with attention, Developmental Neuropsychology, 2001, pp. 445-457, 20.
Hugdahl et. al., Attention and cognitive control: Unfolding the dichotic listening story, Scandinavian Journal of Psychology, 2009, pp. 11-22, 50.
Hugdahl, Kenneth et. al., The effect of stimulus intensity on the right ear advantage in dichotic listening, Neuroscience Letters, 2008, pp. 90-94, 431.
Hunter, Lisa L. et. al., Wideband reflectance in newborns: Normative regions and relationship to hearing-screening results, Ear and Hearing, 2010, pp. 599-610, 31.
International Search Report and Written Opinion issued for PCT/US2017/59297, dated Feb. 1, 2018, 10 pp.
Irvine, D.R.F., Effects of reflex middle-ear muscle contractions on cochlear responses to bone-conducted sound, Audiology, 1976, pp. 433-444, 15.
Katzenell, Udi et. al., Hyperacusis: review and clinical guidelines, Otology &Neurotology, 2001, pp. 321-326, 22.
Keefe, Douglas H. et. al., Ear-canal impedance and reflection coefficient in human infants and adults, The Journal of the Acoustical Society of America, 1993, pp. 2617-2638, 94.
Khalfa et. al., Psychometric normalization of a hyperacusis questionnaire, Orl-Journal for Oto-Rhino-Laryngology, 2002, pp. 436-442, 64, S. Karger AG, Basel.
Khalfa, Stephanie et. al., Increased perception of loudness in autism, Hearing Research, 2004,pp. 87-92,198, Elsevier B.V.
King, Cynthia, Thalamic asymmetry is related to acoustic signal complexity, Neuroscience Letters, 1999, pp. 89-92, 267.
Klin, Ami, Listening preferences in regard to speech in four children with developmental disabilities., Journal of Child Psychology and Psychiatry, 1992, pp. 763-769, 33.
Kofler, Markus et. al, Laterality of auditory startle responses in humans, Clinical Neurophysiology, 2008, pp. 309-314, 119.
Koike, Takuji et. al., Modeling of the human middle ear using the finite-element method, The Journal of the Acoustical Society of America, 2002, pp. 1306-1317, 111.
Kryter, Karl D., Methods for the calculation and use of the articulation index, Journal of the Acoustic Society of America, 1962, pp. 1689-1697, 34.
Lange, Nicholas et. al., Atypical diffusion tensor hemispheric asymmetry in autism,Autism Research, 2010, pp. 350-358, 3.
Tartter, Vivien, Hearing smiles and frowns in normal and whisper registers, The Journal of the Acoustical Society of America, 1994, pp. 2101-2107, 96.
Vallejo, Luis A. et. al., Is the middle ear the first filter of frequency selectivity?, Acta Otorrinolaringologica Espanola 2010, pp. 118-127, 61.
Voss, Susan E. et. al., Measurement of acoustic impedance and reflectance in the human ear canal, Journal of the Acoustic Society of America, 1994, pp. 372-384, 95.
Voyer, Daniel & Ingram, Jennifer D., Attention, reliability, and validity of perceptual asymmetries in the fused dichotic words test, Laterality, 2005, pp. 545-561, 10.

Wang, Yuanqing et. al., An ossified meckel's cartilage in two cretaceous mammals and origin of the mammalian middle ear, Science, 2001, pp. 357-361, 294.
Watson, Linda R. et. al., Behavioral and physiological responses to child-directed speech as predictors of communication outcomes in children with autism spectrum disorders, Journal of Speech, Language, and Hearing Research, 2010, pp. 1-22, 53.
Willi, Urban, The incudo-malleolar joint and sound transmission losses,Hearing Research, 2002, pp. 32-44, 174.
Zwislocki, Jozef, Auditory system: Peripheral nonlinearity and central additivity, as revealed in the human stapedius-muscle reflex, Proceedings of the NationalAcademy of Sciences of the United States of America, 2002, pp. 14601-14606, 99, PNAS.
Levine et. al., The brainstem auditory evoked potential asymmetry is replicable and reliable, Neuropsychologia, 1988, pp. 603-614, 26.
Levine, Robert A. et. al., Right-Left Asymmetries in the Human Brain Stem Auditory Evoked Potentials, Electroencephalography and Clinical Neurophysiology, 1983, pp. 532-537, 55.
Lewis, Gregory F. et al., Statistical strategies to quantify respiratory sinus arrhythmia: Are commonly used metrics equivalent?, Biological Psychology, Dec. 3, 2011, pp. 349-364, vol. 89, SciVerse ScienceDirect.
Liberman, M. Charles et. al., Feedback control of the auditory periphery: anti-masking effects of middle ear muscles vs. olivocochlear efferents, 1998, Journal of Communication Disorders, pp. 471-482, 31.
Lockyer, Linda. et. al., A five to fifteen year follow-up study of infantile psychosis: III. Psychological aspects, The British Journal of Psychiatry, 1969, pp. 86-882, 115.
Lord, Catherine et. al., The autism diagnostic observation schedule—generic: a standard measure of social and communication deficits associated with the spectrum of autism, Journal of Autism and Developmental Disorders, 2000, pp. 205-223, 30.
Lutman, M.E. et. al., Development of an electroacoustic analogue model of the middle ear and acoustic reflex, 1979, Journal of Sound and Vibration, pp. 133-157, 64.
Lutman, M.E., Real-ear calibration of ipsilateral acoustic reflex stimuli from five types of impedance meter, Scandinavian Audiology, 1980, pp. 137-145, 9.
Marco, Elysa et. al., Sensory processing in Autism: A review of Neurophysiologic Findings, Pediatric Research, 2011, pp. 48R-54R, 69, International Pediatric Research Foundation, Inc., USA.
Margolis et. al., Multifrequency tympanometry in normal ears, Audiology, 1985, pp. 44-53,24.
Margolis, Robert H. et. al., Multifrequency tympanometry in normal adults, Ear and Hearing, 1993, pp. 408-413, 14.
Melzack, Ronald, The short-form McGill pain questionnaire, Pain,1987, 30, pp. 191-197, Elsevier.
Mukerji, Sudeep et. al., Auditory brainstem circuits that mediate the middle ear muscle reflex, Trends in Amplification, Sep. 23, 2010, pp. 170-191, 14.
Nageris, Ben I. et. al., Asymmetry in noise-induced hearing loss: relevance of acoustic reflex and left or right handedness, Otology & Neurotology, 2007, pp. 434-437, 28.
Pang, Xiao Dong et. al., Effects of stapedius-muscle contractions on the masking of auditory-nerve responses, Journal of the Acoustic Society of America, 1997, pp. 3576-3586, 102.
Pang, Xiao Dong, Effects of stapedius-muscle contractions on masking of tone responses in the auditory nerve, RLE Technical Report No. 544, Massachusetts Institute of Technology, Research Laboratory of Electronics, Cambridge, Massachusetts, 1989.
Pavlovic, Chaslav V., Derivation of primary parameters and procedure's for use in speech intelligibility predictions, Journal of the Acoustic Society of America, 1987, pp. 413-422, 82.
Perry, William et. al., Sensorimotor gating deficits in adults with autism, Biological Psychiatry, 2007, pp. 482-486, 61.
Pirila, Tapio,"Left-right asymmetry in the human response to experimental noise exposure: Interaural Correlation of the Temporary THreshold SHift at 4 kHz frequency," 1991, Acta oto-laryngologica, 111(5):861-866.
Porges et. al., Reducing Auditory Hypersensitivities in Autistic Spectrum Disorder: Preliminary Findings Evaluating the Listening Project Protocol, Frontiers in Pediatrics, 2014, 2, pp. 1-10.

(56) References Cited

OTHER PUBLICATIONS

Porges et. al., Vagal tone and the physiological regulation of emotion, Monographs of the Society for Research in Child Development, 1994, pp. 167-188, 59.

Porges, S.W. et al., Analyses of periodic processes in psychophysiological research., Cacioppo, J.T., Tassinary, L.G. (Eds.), Principles of Psychophysiology: Physical, Social, and Inferential Elements, 1990, pp. 708-753, Cambridge University Press, New York.

Porges, S.W., The polyvagal theory: phylogenetic substrates of a social nervous system, Int. J. Psychophysiol., 2001, pp. 123-146, 42.

Porges, Stephen et. al., Respiratory sinus arrhythmia and auditory processing in autism: modifiable deficits of an integrated social engagement system, International Journal of Psychophysiology, 2013, pp. 261-270, 88, Elsevier.

Porges, Stephen W., & Lewis, Gregory F., The polyvagal hypothesis: common mechanisms mediating autonomic regulation, vocalizations and listening, Handbook of Behavioral Neuroscience, 2010, pp. 255-264, 19, Elsevier.

Porges, Stephen W., Love: an emergent property of the mammalian autonomic nervous system, Psychoneuroendocrinology, 1998, pp. 837-861, 23, Elsevier Science Ltd., Great Britain.

Porges, Stephen W., Orienting in a defensive world: mammalian modifications of our evolutionary heritage. A polyvagal theory, Psychophysiology, 1995, pp. 301-318, 32.

Porges, Stephen W., Social Engagement and Attachment: A Phylogenetic Perspective, Annals of the New York Academy of Sciences, 2003, pp. 31-47,1008.

Porges, Stephen W., The polyvagal perspective, Biological psychology, 2007, pp. 116-143, 74.

Porges, Stephen W., The vagus: a mediator of behavioral and visceral features associated with autism, The Neurobiology of Autism, 2005, pp. 65-78, Johns Hopkins University Press, Baltimore.

Rhodes, Mark C. et. al., Hearing screening in the newborn intensive care nursery: Comparison of methods, Otolaryngology—Head and Neck Surgery, 1999, pp. 799-808, 120.

Riniolo, Todd C. et. al., Inferential and descriptive influences on measures of respiratory sinus arrhythmia: sampling rate, R-wave trigger accuracy, and variance estimates., Psychophysiology, 1997, pp. 613-621, 34.

Roberts, Brian et. al., The intelligibility of noise-vocoded speech: spectral information available from across-channel comparison of amplitude envelopes, Nov. 10, 2010, Proceedings of the Royal Society B: Biological Sciences, pp. 1595-1600, 278.

Rouiller, Eric M. et. al., Neuronal organization of the stapedius reflex pathways in the rat: a retrograde HRP and viral transneuronal tracing study, Brain Research, 1989,pp. 21-28, 476.

Rowe, Timothy, Coevolution of the mammalian middle ear and neocortex, Science.1996, pp. 651-654, 273, American Association for the Advancement of Science.

Russo et. al., Effects of background noise on cortical encoding of speech in autism spectrum disorders, Journal of Autism and Developmental Disorders, 2009, pp. 1185-1196, 39.

Russo, Nicole et. al., Brainstem transcription of speech is disrupted in children with autism spectrum disorders, Developmental Science, 2009, 557-567,12.

Schutte, Martin et. al., The development of the noise sensitivity questionnaire, Noise and Health, 2007, pp. 15-24, 9.

Seibert, J. M., Hogan, A. E., Mundy, P.C, Assessing interactional competencies: the early social-communication scales, Infant Mental Health Journal, 1982, 244-58, 3.

Shahnaz, Navid & Polka, Linda, Standard and multifrequency tympanometry in normal and otosclerotic ears, Ear and Hearing, 1997, pp. 326-341, 18, Williams & Wilkins.

Shrout, Patrick E., Measurement reliability and agreement in psychiatry, Statistical Methods in Medical Research, 1998, pp. 301-317, 7.

Simmons, F. Blair et. al., A theory of middle ear muscle function at moderate sound levels, Science, 1962, pp. 590-592, 138.

Sininger et. al., Comment on 'ear asymmetries in middle-ear, cochlear, and brainstem responses in human infants, 2008, Journal of the Acoustic Society of America, pp. 1401-1403, 124.

Sininger et. al., Lateral asymmetry in the ABR of neonates: evidence and mechanisms, Hearing Research, 2006, pp. 203-211, 212.

Sininger, Y.S. et. al., Asymmetric cochlear processing mimics hemispheric specialization, Science, 2004, 1581, 305.

Spearman, C., Correlation calculated from faulty data, British Journal of Psychology, 1910, pp. 271-295, 3.

Stansfeld, Stephen A., Sharp, Don, Gallacher, John, Noise, noise sensitivity and psychiatric disorder: epidemiological and psychophysiological studies, Psychological Medicine. Supplement, 1992, pp. 1-44, 22.

Stenfelt, Stefan, Middle ear ossicles motion at hearing thresholds with air conduction and bone conduction stimulation,2006, Journal of the Acoustic Society of America, pp. 2848-2858, 119.

Summers, Robert J., Bailey, Peter J., & Roberts, Brian, Effects of differences in fundamental frequency on across-formant grouping in speech perception, 2010, The Journal of the Acoustical Society of America, pp. 3667-3677, 128.

Suzuki, Yoiti et. al., Equal-loudness-level contours for pure tones, 2004, Journal of the Acoustic Society of America, pp. 918-933, 116.

\* cited by examiner

SYSTEMS AND METHODS FOR MODULATING PHYSIOLOGICAL STATE

CROSS-REFERENCE TO RELATED APPLICATIONS

The present application claims benefit of U.S. provisional patent application No. 62/637,251, titled "Systems and Methods for Modulating Physiological State," filed Mar. 1, 2018, which is incorporated by reference herein in its entirety.

BACKGROUND

Conventional body-monitoring systems employ sensors to measure one or more variables relating to physiological signals produced by an individual's body. These systems typically output information relating to measured variables such that the individual or a healthcare provider responsible for the individual may monitor the information and take any necessary actions to achieve an objective.

Body-monitoring systems often monitor the same or similar variables for a plurality of objectives. As an example, blood pressure may be monitored and displayed (e.g., in time series) in a critical care medical environment such that a physician may intervene when the variable indicates a health risk. As another example, an individual may monitor their own blood pressure in a home environment in order to take a precautionary action, such as ingesting a medicine, resting, changing their diet and/or exercising. And, as yet another example, an individual may monitor their heart rate during physical activity to adjust pace or resistance.

In each of the above examples, an individual (i.e., the user or a surrogate) must take an action in response to the monitored variable. From a systems perspective, these examples represent open-loop systems because they require an individual to be an active part of the feedback loop.

With the development of new processing and sensor technologies, biotechnology companies are developing closed-loop systems and devices to monitor and automatically regulate physiological processes. Unfortunately, the sensors employed by such systems cannot monitor component neural influences embedded in monitored bio-signals. As a result, these systems often provide feedback conveying a poor approximation of the signal that the nervous system is anticipating.

Bio-signals produced by visceral organs and other body or brain structures are complex and usually represent a composite of several underlying mechanisms, including endocrine and neural influences. Although the sensors employed in currently-available, closed-loop systems may accurately detect level, the surveillance pathways embedded in the nervous system (i.e., afferent pathways that convey information about target organs to brainstem regulatory mechanisms) may be sensitive to the characteristics of the temporal pattern of change (i.e., the temporal window during which changes—including levels and complex periodic and aperiodic patterns—are induced). Accordingly, feedback that changes level in the process, signal, or variable being monitored (e.g., delivery of a pharmaceutical or neurostimulation) may inadvertently distort, rather than optimize, the desired trajectory. Without being knowledgeable that the nervous system incorporates circuits that may functionally anticipate a physiological signature (i.e., a neurophysiologically informed pattern), well-intentioned, closed-loop designs may inappropriately shift levels of a target system causing disruption to the nervous system.

For example, manipulations that change slope and level of a relatively stable signal will introduce quasi-periodic components into the time series. The resulting quasi-periodic time series will have statistical characteristics that distinguish it from the more sinusoidal, rhythmic patterns observed in well-regulated, physiological systems that characterize many homeostatic processes. Moreover, although an induced quasi-periodic time series may have a physiologically relevant, fundamental oscillation, it may also include higher frequency harmonics that convey non-relevant physiological information.

As patterns deviate from the more rhythmic neurophysiological expectations, the neurophysiological sensors embedded in the mammalian nervous system are less likely to be able to decode the meaning of these sources of variance. Thus, the deviations from expectations may confuse the endogenous sensors embedded in the nervous system that evolved to regulate these systems and to maintain homeostatic function to optimize health, growth, and restoration. In contrast to a surveillance of shifts in levels, the nervous system may expect a more complex signal including a combination of periodic oscillations of varying amplitudes, periodicities, and slopes.

Accordingly, there is a need for closed-loop systems that are adapted to monitor and automatically regulate physiological structures and that employ efficient and accurate feedback indexing the dynamically changing neural influences on the monitored physiological structures. It would be beneficial if such systems were adapted to shift neural regulation of a specific physiological structure and/or a more general physiological state of a subject to promote and influence emergent properties that support various outcomes relating to, for example, health, positive affect, alertness, spontaneous interactions with others, attentiveness, mental effort and/or physical exertion.

SUMMARY

In accordance with the foregoing objectives and others, exemplary methods, systems and apparatuses are provided to monitor bio-signals associated with one or more physiological structures of a subject. The embodiments may employ neural processing to determine neural information embedded within the bio-signals. Such neural information may be utilized to determine a current state of the subject and appropriate feedback that may be provided to the subject to shift neural regulation of at least one of the monitored structures. The feedback may be in the form of stimulation having a complex signal including a combination of periodic oscillations of varying amplitudes, periodicities, and slopes. And the feedback may be automatically transmitted to the subject in order to modify the subject's current state to a desired state that supports a particular outcome.

In one embodiment, a method is provided. The method may include receiving bio-signal information relating to bio-signals associated with a monitored physiological structure of a subject; determining neural information from the bio-signal information; and determining a current state of the subject based on the neural information. Upon determining that the current state is different than a desired state, feedback to be provided to the subject may be determined, based on the current state and the desired state; and the determined feedback may be provided to the subject to thereby modify neural regulation of the monitored physiological structure of the subject. In one embodiment, the above steps may be repeated until the current state is substantially similar to the desired state or a predetermined termination events occurs (e.g., a time period expires).

In another embodiment, a neural processing method is provided. The method may include receiving, by a neural sensor, from a biomonitoring device, bio-signal information relating to bio-signals associated with a monitored physiological structure of a subject; extracting, by the neural sensor, one or more neural indices from the bio-signal information; determining, by the neural sensor, one or more neural metrics from at least one neural index of the one or more neural indices; and/or transmitting, by the neural sensor, to an integrator/regulator, neural information that includes the one or more neural indices and the one or more neural metrics. In certain cases, each of the one or more neural indices may relate to neural regulation, via an identifiable neural pathway, of the monitored physiological structure.

In one embodiment, each of the one or more neural metrics may relate to a property of the at least one neural index, such as amplitude, level, phase, slope and frequency. In such cases, each of the one or more neural metrics may include a time series associated with a plurality of time periods during which the property is quantified.

In another embodiment, the above method may also include determining, by the neural sensor, one or more patterns relating to at least one of the neural metrics time series. The method may also include determining, by the neural sensor, one or more covariations among the neural metrics. Such covariations may relate to, for example, phase, slope and/or coupling.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Various systems, methods and apparatuses are disclosed herein to monitor and automatically regulate one or more physiological structures of a subject. Generally, the disclosed embodiments may monitor bio-signals relating to one or more structures of a subject; process the bio-signals to determine neural information contained therein; determine a current state of the subject (e.g., based on the neural information); determine feedback to be provided to the subject based on the current state and a desired state; and/or provide the feedback to the subject in order to modify neural regulation of at least one of the monitored structures (e.g., through a neurophysiological sensory portals) such that the subject's state is modified from the current state to the desired state.

The embodiments may employ improved feedback loops that utilize neural information comprising accurate neural metrics indexing specific neural influences on a monitored physiological structure. The systems may extract neural information from bio-signals and employ such information to determine appropriate feedback and an optimal means of providing such feedback to the subject (e.g., to the subject's nervous system and/or particular brain structures involved in regulating a monitored structure). The described embodiments may be adapted to dynamically modify feedback over time, based on detected changes in the neural information associated with the monitored structure(s) (e.g., in response to the provided feedback).

In certain embodiments, one or more sensors may be employed to receive and/or determine information relating to stimuli present within a subject's environment or context. In such cases, the embodiments may take such information into account when determining appropriate feedback and/or may provide the feedback to the subject by manipulating environmental stimuli.

System

Figure 1:
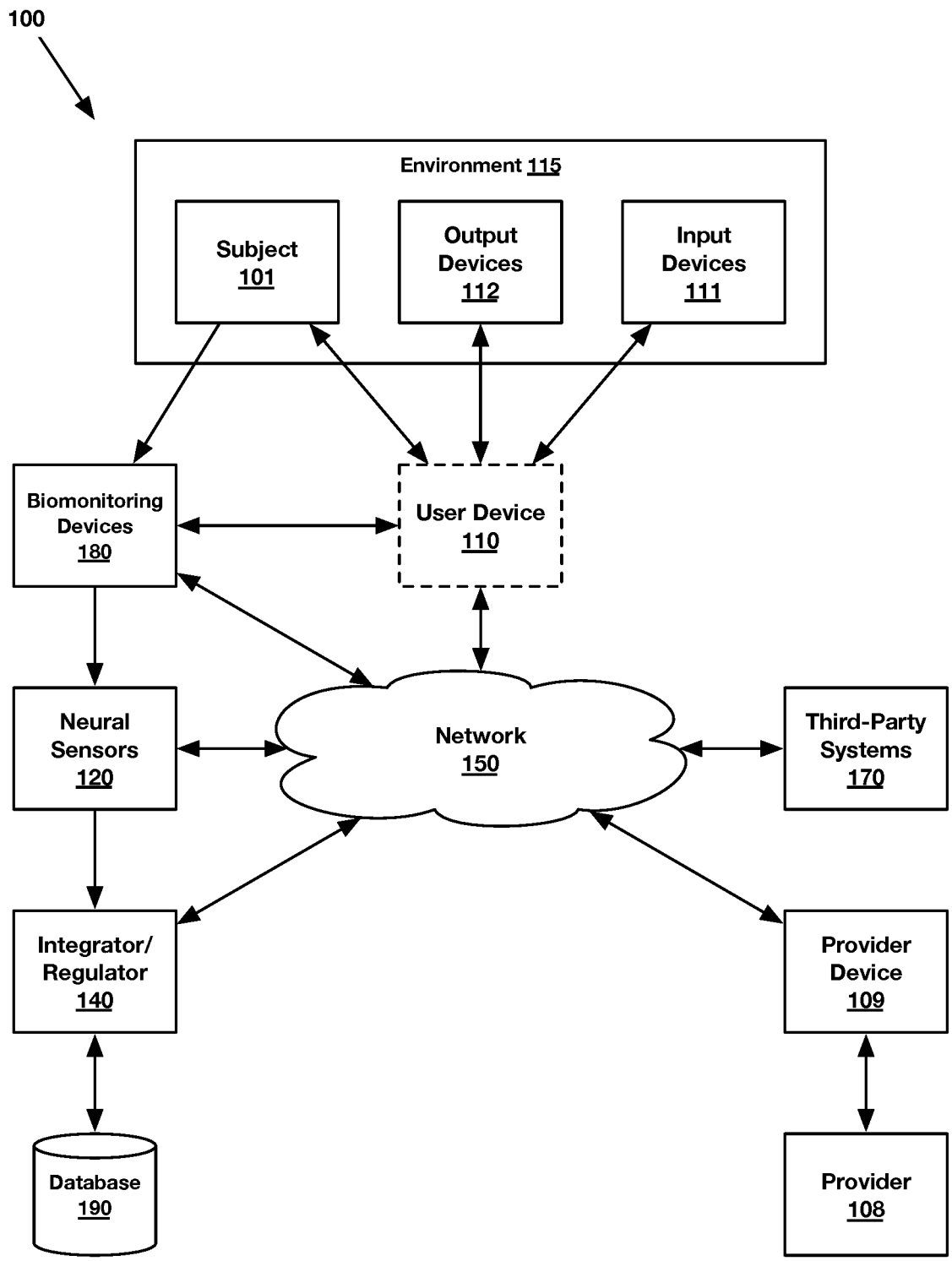
FIG. 1 shows an exemplary system 100 according to an embodiment.

Referring to FIG. 1, an exemplary system 100 is illustrated. The system 100 may include a user device 110 accessed by a subject 101, a provider device 109 accessed by a provider 108, biomonitoring devices 180, neural sensors 120, input devices 111 and/or output devices 112, each of which may be in communication with a network 150 (e.g., Internet, intranet, local-area network ("LAN"), wide-area network ("WAN"), cellular, etc.). In certain embodiments, one or more of the biomonitoring devices 180, input devices 111 and/or output devices 112 may additionally or alternatively be in communication with, or integrated into, the user device 110.

As shown, the system 100 includes an integrator/regulator 140, which may also be in communication with the network 150. The integrator/regulator 140 may be adapted to receive, determine, record and/or transmit user information relating to any number of subjects 101. The integrator/regulator 140 may store received or determined user information in, for example, a database 190.

Generally, user information may include, but is not limited to: bio-signals; neural information; state information; outcome information; environment information; feedback information; identification information (e.g., name, age, date of birth, sex, social security number, unique patient ID, room number, photo, etc.); contact information (e.g., email address, physical address, phone number, etc.); insurance and billing information (e.g., insurance provider, account number, credit card information, billing address, etc.); employment information; and/or medical information (e.g., current and/or historical conditions, medications, examinations, treatments, procedures, allergies, immunizations, dietary restrictions, genetic diseases etc.).

In one embodiment, the integrator/regulator 140 may receive bio-signals from a biomonitoring device 180 monitoring a subject 101 (e.g., directly or indirectly via the network 150). The term "bio-signal" relates to body processes and/or peripheral physiological signals produced by visceral organs and other body or brain structures (individually and collectively referred to herein as "physiological structures" or "structures") that may be detected and/or continually measured/monitored by a biomonitoring device 180. Bio-signals may represent bioelectrical, biophysical, or biochemical changes produced by one or more of a subject's 101 structures. In certain cases, bio-signals may be transduced through the physics of the subject's body to a signal that is manifest in changes on the surface of the subject's body.

Generally, the system may measure and monitor electrical, mechanical, acoustic, chemical and/or optical bio-signals. Examples of such bio-signals include, but are not limited to: heart rate or pulse rate, respiratory rate, blood pressure, cardiac rhythm, oxygen saturation, pH, pulse wave slope, pulse wave amplitude, vascular tone, electromagnetic fields from bodily organs, sudomotor activity, ECG, electrogastrogram ("EGG"), electroencephalogram ("EEGs"), electromyogram ("EMG"), electrooculography ("EOG"), electrodermal activity ("EDA"), galvanic skin response ("GSR"), skin potential or other electrical activity from a body surface, mechanomyogram ("MMG"), endocrine levels, immune reactions (e.g., antibodies), cerebral spinal fluid properties and/or pressure, pupil diameter, vocalizations, movements, body temperature, height, weight, body mass index ("BMI"), hydration, and/or blood glucose level. It will be appreciated that bio-signals may represent a composite of several underlying components, sources and/or influences, such as endocrine influences, neural influences, sensor noise, biological noise and/or measurement error.

As shown, the integrator/regulator 140 may employ one or more neural sensors 120 to determine neural information relating to bio-signals. The term "neural information" refers to components of a bio-signal that represent validated neural indices of the dynamic regulation of monitored structures via identifiable neural pathways and/or neural metrics quantified from such neural indices. As an example, sensory and motor pathways of the autonomic nervous system and endocrine system regulate visceral organs through changes in pattern that are frequently reflected in the amplitude, slope, and period of oscillatory process. Accordingly, neural indices may be manifested in bio-signals as periodicities and quasi-periodicities.

As detailed below, each of the neural indices may comprise metrics that can be quantified over short periods to produce a continuous and dynamically changing array of neural metrics (i.e., a neural metrics time series). Exemplary neural metrics may relate to one or more of: amplitude, level, phase, slope, and/or time period (i.e., frequency). Amplitude may convey information about degree or strength of neural tone to a monitored structure. Phase may provide information about the slope of a rising and falling signal. And the time period may reflect the time constant of the neural feedback on the structure.

State information relates to a current or desired physiological, emotional, affective, and/or behavioral state of a subject 101. Physiological states generally relate to properties of specific structures, such as an output of a visceral organ. For example, a physiological state may be characterized by a vagal withdrawal. As another example, a physiological state may be characterized by increased vagal influence on the heart (e.g., via pathways originating in the nucleus ambiguus).

Emotional and affective states generally relate to emotions or feelings that may influence a subject's physiology or behavior (e.g., agitation, alertness, anxiousness, anger, arousal, calmness, nervousness, sickness, tiredness, and/or being upset). And behavioral states generally relate to a subject's relationship with one or more activities/behaviors (e.g., sleeping, resting, relaxing, meditating, concentrating or otherwise engaging in a mental activity, speaking or otherwise engaging in a social interaction, and/or exercising or otherwise engaging in a physical activity). A subject's relationship with a behavior/activity may relate to, for example, a particular behavior exhibited by a subject, a subject's ability to regulate or control a specific behavior, a particular activity performed or attempted by a subject, a subject's ability level with respect to performance of a particular activity, a subject's ability to refrain from participating in a particular activity, a subject's enjoyment of a particular activity and/or a subject's dislike of a particular activity.

As discussed in detail below, the system may be adapted to dynamically determine a subject's 101 current state based only on determined neural information. Alternatively, the system may utilize determined neural information and additional information (e.g., received bio-signals, user input, etc.) to determine the subject's current state.

In one embodiment, the system may receive a desired state from a user (e.g., a subject 101 or a provider 108). However, in other embodiments, the system may determine a desired state based on a received or pre-determined desired outcome.

It will be appreciated that a given state may differentially and selectively support a particular outcome. For example, as discussed below, a state characterized by a vagal withdrawal would support mobilization behaviors (e.g., fight and flight). In contrast, a state characterized by increased vagal influence (e.g., via pathways originating in the nucleus ambiguus) on the heart, would support spontaneous social engagement behaviors.

An outcome is generally associated with a desired, acute (i.e., transitory) or permanent (i.e., chronic) objective relating to a subject, such as a physiological, medical, behavioral, cognitive, and/or affective (i.e., emotional) objective. For example, various outcomes may relate to increasing, decreasing, improving, and/or optimizing one or more of: attentiveness, mental effort, cognitive ability, health, growth, restoration, recovery following illness or injury, performance of a physical activity (e.g., standing, walking, running, stretching, moving, strength training, playing a sport, etc.), social engagement (e.g., spontaneous interaction with others), ability to eat or drink, vocalization, relaxation, meditation, sleep and/or waking from sleep. Additionally or alternatively, an outcome may relate to minimum, maximum, average and/or median activity of a subject over a given time period.

Generally, the integrator/regulator 140 may receive outcome information relating to a desired outcome for the subject 101 from a user. For example, such information may be input by a subject 101 via a user device 110 and/or may be input by a provider 108 via a provider device 109).

In certain embodiments, the integrator/regulator 140 may receive or determine environment information relating to stimuli present within an environment 115 of the subject 101, such as acoustic stimuli, visual stimuli, tactile stimuli and/or olfactory stimuli. As discussed below, environmental stimuli have the potential to "trigger" physiological responses in the subject 101 that may hinder or support modification of a subject's state to a desired state.

The integrator/regulator 140 may determine feedback information relating to appropriate feedback (e.g., stimuli) that may be provided to a subject 101 in order to modify the subject's current state to a desired state that supports a particular outcome. As discussed in detail below, the integrator/regulator 140 may determine appropriate feedback to be provided to the subject 101 based on bio-signals, neural information determined from such bio-signals, the subject's current state, a desired state and, optionally, any environment information. The integrator/regulator 140 may provide the determined feedback directly to the subject 101 and/or indirectly via one or more connected components (e.g., an output device 112 and/or a user device 110).

Client Devices

As shown, the system 100 may include one or more client devices, such as a user device 110 accessed by a subject 101 and/or a provider device 109 accessed by a provider 108. Generally, a client device 109, 110 may be any device capable of running an online, mobile or desktop client application and/or of accessing the integrator/regulator 140 (e.g., via a network 150) to allow a user to create, access, update and/or delete user information. Exemplary client devices may include general-purpose computers, special-purpose computers, desktop computers, laptop computers, smartphones, tablets, virtual reality devices and/or wearable devices.

In certain embodiments, user information may be manually entered or selected via a user device 110 and/or the provider device 109. The user information may additionally or alternatively be received from and/or transmitted to the integrator/regulator 140 (e.g., a backend application running on the integrator/regulator). Moreover, any of such user information may be stored in and/or retrieved from one or more local or remote databases 190.

Biomonitoring Devices

The system 100 may include any number of portable, wearable, implantable and/or stationary biomonitoring devices 180 adapted to receive or determine bio-signals relating to a subject 101. To that end, each of the biomonitoring devices 180 may comprise one or more contact sensors (i.e., sensors in direct physical contact with the subject's 101 body) and/or noncontact sensors (i.e., sensors that do not contact the subject's body).

Exemplary contact sensors may include electrodes or other means adapted to detect electrical bio-signals from the subject's heart (e.g., ECG) and/or other body structures (e.g., electrogastrogram, electromyogram, electroencephalogram, etc.). Additionally or alternatively, contact sensors may be adapted to detect bio-signals relating to one or more processes/activities. For example, an accelerometer may be employed to measure a time series of the subject's body movements, which may include be influenced by autonomic function.

Exemplary noncontact sensors may include photosensors, acoustic sensors, and/or other sensors adapted to receive/determine bio-signals relating to dynamic changes in energy reflection and absorption of the subject's body (or a particular structure thereof) at one or more wavelengths. For example, a photosensor may function as a noncontact PPG to obtain a signal reflecting vascular processes including pulse wave activity from the subject's face. As another example, a noncontact photosensor sensor may be employed to monitor the subject's pupillary oscillations, eye movements and/or other physiological activity.

In one specific embodiment, a microphone may be employed as a noncontact sensor to monitor a subject's 101 vocalizations. Such vocalizations can be conceptualized as a composite bio-signal containing acoustic components reflecting specific neural mechanisms. The neural information conveyed via voice reflects features relating to the neural regulation of the autonomic nervous system (e.g., features that are similar to those that may be measured with ECG sensors and/or a PPG sensors). A model describing the features in mammalian vocalizations has been outline in the Polyvagal Theory and is described in the following references, each of which is incorporated by reference herein in its entirety: Porges, S. W., "The polyvagal perspective," Biological Psychology, 2007, 74(2), 116-143; Porges S. W., "The Polyvagal Theory: Neurophysiological Foundations of Emotions, Attachment, Communication, and Self-regulation," 2011, New York: WW Norton; Porges, S. W., & Lewis, G. F., "The polyvagal hypothesis: common mechanisms mediating autonomic regulation, vocalizations and listening," 2010, in Handbook of Behavioral Neuroscience, Vol. 19, pp. 255-264, Elsevier; and Kolacz J. et al., "The integration of vocal communication and biobehavioral state regulation in mammals: A polyvagal hypothesis," 2018, in S. M. Brudzynski, ed. Handbook of Ultrasonic Vocalization, Amsterdam: Academic Press.

It will be appreciated that biomonitoring devices 180 may comprise any number of sensors, including contact and/or noncontact sensors of multiple types, for measuring and/or determining bio-signals. Exemplary sensors that may be integrated into, or otherwise placed in communication with, biomonitoring devices 180 are listed below in Table 1.

TABLE 1

Biomonitoring Device Sensors

| Sensor | Information | Use |
|---|---|---|
| Accelerometer | Linear acceleration and orientation | activity detection; sleep detection; seizure activity |
| Gyroscope | angular rotational velocity across three axes | activity detection; sleep detection; respiratory rate and pattern |
| Pedometer | steps taken by subject | activity detection; sleep detection |
| Magnetometer | orientation | activity detection; sleep detection |
| Proximity Sensor | proximity of nearby objects with respect to the subject or a user device | output device activation or adjustment; localization |
| Gravity Sensor | gravity (relative or absolute) | activity detection; sleep detection |
| Pressure Sensor | ambient pressure (relative or absolute) | activity detection; sleep detection |
| Moisture Sensor | ambient or subject moisture (relative or absolute) | liquid detection; ambient humidity; washing detection |
| Temperature Sensor | ambient or subject temperature (relative or absolute) | temperature; activity detection; sleep detection |
| Light Sensor | ambient light (relative or absolute) | display and/or LED activation and settings |
| Heart Rate/ Rhythm Sensors | subject heart rate and rhythm | activity detection; sleep detection; heart rate and rhythm; ECG, EMG, EEG, or respiration; ballistic force |
| Pulse Oximetry | subject oxygen (and other blood gas) saturation | activity detection; sleep detection; heart rate; oxygen saturation |
| Hydration Sensor | subject hydration | patient hydration; stress response; electrolyte monitoring |
| Radiation Sensor | radiation | radiation dosage; radiation emission |
| Drug Sensors | amount of drug in a subject's system | drug concentration; proper drug dosing |
| Carbon Dioxide ($CO_2$) Sensor | $CO_2$ concentration; $CO_2$ exhaled | transcutaneous CO2; endotracheal tube placement confirmation; sedation; respiratory state; partial arterial pressure of CO2 |

TABLE 1-continued

Biomonitoring Device Sensors

| Sensor | Information | Use |
|---|---|---|
| Electrical Conductivity Sensor | skin conductivity | skin conductance (electrodermal) response; sympathetic activity |
| Camera | visual | facial recognition; vascular activity/tone; pupillary activity; eye movement; pulse activity |
| Microphone | audio | acoustic features in voice; neural (vagal) control of the heart; heart rate and rhythm detection |

In addition to sensors, biomonitoring devices 180 may also include one or more processors (or microprocessors). For example, an independent application processor may be used to store and execute applications that utilize sensor data acquired and/or processed by one or more sensor processors (i.e., processor(s) that process data from contact and/or noncontact sensors). In the case where a biomonitoring device includes multiple sensors, the device may also include multiple sensor processors. An application processor may have sensors directly connected to it as well. Sensor and application processors may exist as separate discrete chips or may exist within the same packaged chip (i.e., multi-core).

Each biomonitoring device 180 may also include internal or external memory in communication with the processor(s) and/or sensor(s), such as but not limited to, read-only memory ("ROM") (e.g., NAND flash, NOR flash, flash on another processor, other solid-state storage, mechanical or optical disks) and/or random-access memory ("RAM"). The memory may store executable code or instructions for one or more applications. When an application is requested to be executed, the processor retrieves corresponding executable code and/or data from the memory and executes it. The executable code can be temporarily or permanently stored on the memory or storage of the application processor.

The biomonitoring devices 180 may comprise one or more transceivers to allow for received/determined bio-signals to be transmitted to one or more of the neural sensors 120, the integrator/regulator 140, the user device 110 and/or other biomonitoring devices (e.g., directly or indirectly via the network 150). The transceivers may also allow the biomonitoring devices 180 to receive real-time or stored information from such system components (e.g., directly or indirectly via the network 150). Exemplary transceivers may include, but are not limited to: Bluetooth transceivers, Bluetooth Low Energy ("BLE") transceivers, Near Field Communication ("NFC") transceivers, infrared transceivers, radio-frequency identification ("RFID") transceivers, ZIGBEE transceivers, Z-WAVE transceivers, satellite transceivers (e.g., GPS), WIFI transceivers, cellular transceivers (e.g., CDMA or GSM-type cellular antennas) and others.

It will be appreciated that, in some cases, a user device 110 may itself be considered a biomonitoring device 180. For example, a wearable device, smartphone or tablet may comprise a plurality of sensors that may measure and/or determine bio-signals. Additionally, such devices may comprise a plurality of transceivers that may be employed to transmit/receive bio-signal information to/from various system components.

Neural Sensors

As shown in FIG. 1, the system 100 may include one or more neural sensors 120 in communication with the integrator/regulator 140 (e.g., directly and/or indirectly via the network 150). The neural sensors 120 are generally adapted to receive bio-signals from the biomonitoring device 180, dynamically extract neural information from such bio-signals via complex and neurophysiologically informed algorithms and hardware design, and provide the neural information to the integrator/regulator 140.

As discussed below in reference to FIGS. 3-4, the neural sensors 120 generally extract component neural information from received bio-signals by applying algorithms informed by knowledge of neural circuits (e.g., biological feedback systems with time constants reflected in the periodicity of oscillations and slopes associated with pulsatile activity). Such knowledge informs the development and modification of neural sensors, the physics of the neural sensor, and the quantitative (mathematical and statistical) procedures applied by the neural sensors to extract neural information embedded within the bio-signals. This approach enables the neural sensors 120 to uniquely and accurately monitor the output of neural and neurochemical pathways involved in optimizing the function of peripheral physiology to evaluate the consequences that might evolve when feedback is provided to the subject.

The neural sensors 120 may each include one or more processors (or microprocessors). For example, an independent application processor may be used to store and execute applications that utilize sensor data acquired from a biomonitoring device 180 and/or processed by one or more sensor processors. In the case where there are multiple biomonitoring devices 180 and/or where a single biomonitoring device comprises multiple sensors, each neural sensor 120 may comprise multiple sensor processors. An application processor may have biomonitoring device sensors directly connected to it as well. The sensor and application processors may exist as separate discrete chips or exist within the same packaged chip (i.e., multi-core).

Each neural sensor 120 may also include internal or external memory in communication with the processor(s), such as but not limited to, ROM and/or RAM. The memory may store executable code or instructions for one or more applications. When an application is requested to be executed, the processor retrieves corresponding executable code and/or data from the memory and executes it. The executable code can be temporarily or permanently stored on the memory or storage of the application processor.

Finally, each of the neural sensors 120 may comprise one or more transceivers, such as but not limited to: Bluetooth transceivers, BLE transceivers, NFC transceivers, infrared transceivers, RFID transceivers, ZIGBEE transceivers, Z-WAVE transceivers, satellite transceivers (e.g., GPS), WIFI transceivers, cellular transceivers (e.g., CDMA or GSM-type cellular antennas) and others. Such transceivers may be employed to send and/or receive real-time or stored information to/from biomonitoring devices 180, the integrator/regulator 140 and/or the user device 110 (e.g., directly or indirectly via the network 150).

It will be appreciated that the neural sensors 120 are not limited to the specific applications discussed herein. Indeed, such neural sensors 120 may be employed to improve efficiency and accuracy of any system or device that monitors bio-signals.

Input & Output Devices

The system may further comprise any number of input devices 111 and/or output devices 112. Such devices may be in communication with the subject 101 and/or the subject's environment 115 in order to measure, determine, modify and/or generate various stimuli. It will be appreciated that the input devices 111 and/or output devices 112 may be in direct communication with the integrator/regulator 140 or may be indirectly connected thereto via the network 150. Moreover, one or more input devices 111 and/or output devices 112 may be connected to, or integrated within, a user device 110 in communication with the integrator/regulator 140 (e.g., directly or indirectly via the network 150).

Generally, output devices 112 may be adapted to provide discreet stimuli to a subject 101 (e.g., acoustic, visual, tactile and/or olfactory stimuli) and/or to modify environmental stimuli present within the subject's environment 115 (e.g., temperature, moisture, sound, light, etc.). Exemplary output devices 112 may include, but are not limited to, speakers, headphones, circumaural headphones, earphones, vibration motors, displays, lights, virtual reality devices, heating and/or cooling systems, humidifiers, scent diffusers, and/or others.

As an example, an audio device may be employed to play recorded and/or streaming acoustic stimuli within the environment 115. As another example, an audio/video device may be employed to output acoustic stimuli to the subject with synchronized visual stimuli (e.g., video). And as yet another example, a wearable device comprising a vibration motor may be employed to provide tactile stimuli to the subject.

The system may further comprise any number of input devices 111 adapted to receive and/or determine information relating to any stimuli present within the environment 115. For example, the system may comprise any number of microphones, cameras or other light sensors, temperature sensors, gravity sensors, olfactory sensors, and/or moisture sensors. As another example, the system may comprise one or more actuators, controls, buttons, pointing devices and/or touchscreens to receive manual input from the subject 101.

In one specific embodiment the system may comprise an input device 111 having a microphone. In such embodiment, an acoustic input signal output by an audio output device 112 and/or the subject 101 may be received by the microphone input device 111. The received audio input signal may be transmitted by the input device 111 to the integrator/regulator 140, where it is modulated according to determined feedback information and then transmitted to the audio output device 112 (or a separate output device). The modulated audio signal may then be output by the output device such that it may be heard by the subject. It will be appreciated that such processes may occur in real time or near-real time.

Although not shown, the system 100 may optionally include a gateway that is adapted to receive information from one or more of the biomonitoring devices 180, output devices 112, input devices 111, and/or neural sensors 120 (e.g., via Bluetooth, BLE, NFC, RFID, ZIGBEE, Z-WAVE, CDMA and/or GSM) and transmit such information to the integrator/regulator 140 (e.g., via the network 150). The gateway may be further adapted to receive information from the integrator/regulator 140 (e.g., via WIFI and/or Ethernet) and transmit such information to one or more of the biomonitoring devices 180, output devices, input devices 111, and/or neural sensors 120 (e.g., via Bluetooth, BLE, NFC, RFID, ZIGBEE, Z-WAVE, CDMA and/or GSM).

In an alternative embodiment, the functionality of a gateway may be incorporated into a user device 110. In this embodiment, one or more of the biomonitoring devices 180, output devices 112, input devices 111, and/or neural sensors 120 may be configured to communicate with the user device 110 through a first wireless protocol (e.g., Bluetooth or BLE) and the user device may be configured to communicate with the integrator/regulator 140 through a second wireless protocol (e.g., WIFI or cellular).

In one embodiment, the system 110 may further comprise one or more third-party systems 170 connected to the integrator/regulator 140, for example, via the network 150. Third-party systems 170 may store information in one or more databases that may be accessed by the integrator/regulator 140. Exemplary third-party systems 170 may include, but are not limited to: electronic medical record systems and other healthcare provider systems; financial or insurance systems (e.g., billing, invoicing, and/or accounting systems); contact management systems; customer relationship management ("CRM") systems; project and/or task management systems; calendaring and/or scheduling systems; backup systems; communication systems and/or others.

The integrator/regulator 140 may be capable of retrieving and/or storing information from third-party systems 170, with or without user interaction. Moreover, the integrator/regulator 140 may be capable of communicating stored information to third-party systems 170, and may notify users of such communications.

It will be appreciated that, although the biomonitoring devices 180, neural sensors 120, input devices 111, output devices 112, user devices 110 and integrator/regulator 140 are shown as separate components in the illustrated system 100, two or more of these components may be combined or integrated into a single computing system in other embodiments. For example, a user device, such as a smartphone or laptop computer, may comprise one or more biomonitoring devices 180 (e.g., a camera), one or more input devices 111 (e.g., a keyboard, touchscreen and/or a microphone) and one or more output devices 112 (e.g., a display, a vibration motor, speakers and/or connected headphones). Such user device may be connected to a backend computing system that comprises one or more neural sensors 120 and the integrator/regulator 140. Alternatively, the user device may itself provide the functionality of the neural sensors and integrator/regulator via an included processor and internal memory.

Integrator/Regulator

Figure 2:
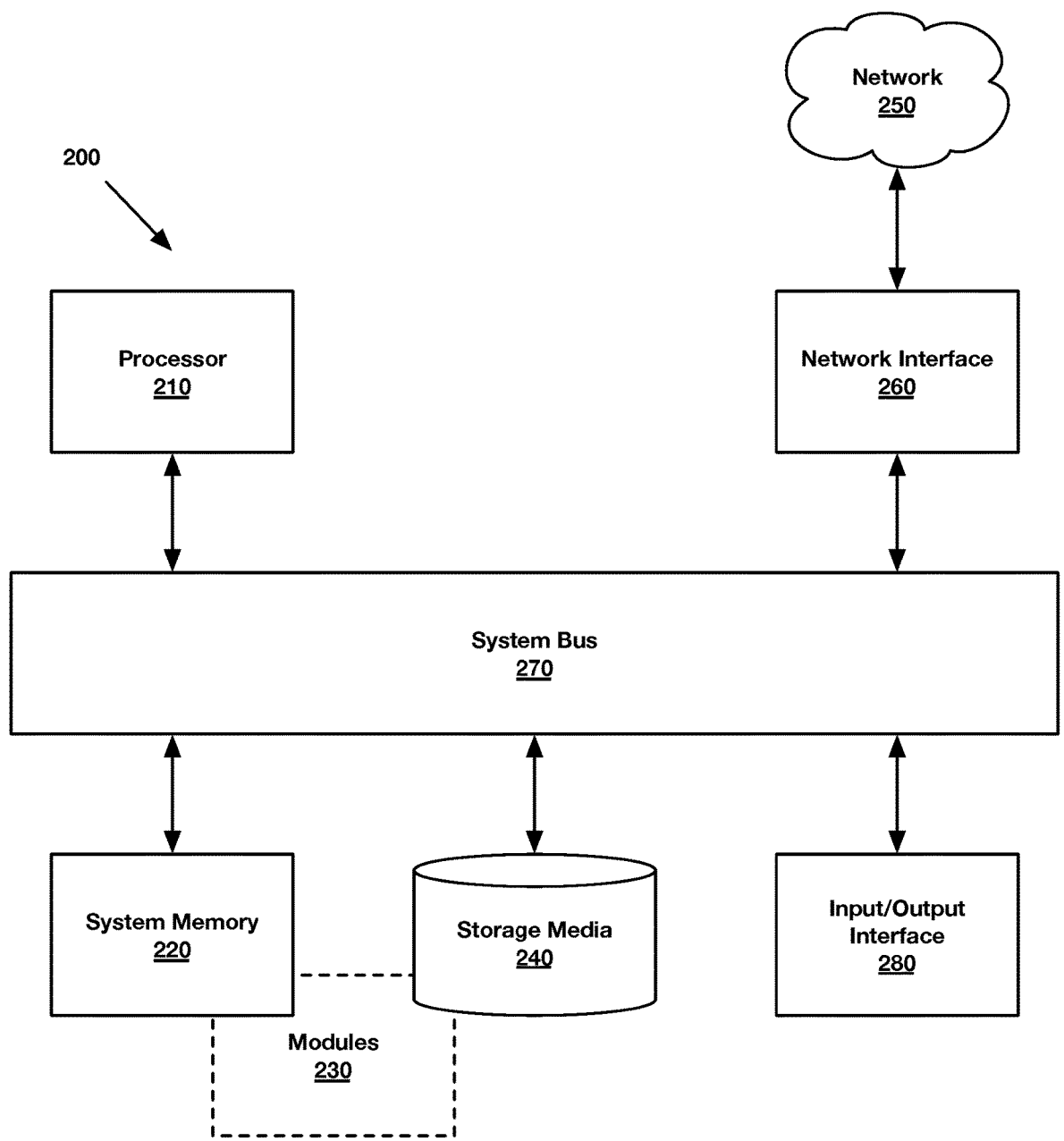
FIG. 2 shows an exemplary integrator/regulator 200 according to an embodiment.

Referring to FIG. 2, a block diagram is provided illustrating an exemplary integrator/regulator 200 in accordance with one or more embodiments presented herein. The integrator/regulator 200 may correspond to the interrogator/regulator 140 shown in FIG. 1 and/or any of the various user devices, provider devices, biomonitoring devices, neural sensors, input devices, output devices, embedded systems, and/or other computing systems presented herein.

Generally, the integrator/regulator 200 may include various internal and/or attached components such as a processor 210, a system bus 270, system memory 220, storage media 240, modules 230 an input/output interface 280, and a network interface 260 for communicating with a network 250. The integrator/regulator 200 may be implemented as a conventional computer system, an embedded controller, a laptop, a server, a mobile device, a smartphone, a kiosk, one or more processors associated with a display, a customized machine, any other hardware platform and/or combinations thereof. And, in some embodiments, the integrator/regulator 200 may be a distributed system configured to function using multiple computing devices interconnected via a data network or system bus 270.

The processor 210 may be configured to execute code or instructions to perform the operations and functionality described herein, manage request flow and address mappings, and to perform calculations and generate commands. Generally, the processor 210 may be configured to monitor and control the operation of the components in the integrator/regulator 200. To that end, the processor 210 may be a general-purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 210 may be a single processing unit, multiple processing units, a single processing core, multiple processing cores, special purpose processing cores, coprocessors, or any combination thereof. According to certain embodiments, the processor 210 and/or other components of the integrator/regulator 200 may be a virtualized server executing within one or more other servers.

The system memory 220 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 220 also may include volatile memories, such as RAM, static random-access memory ("SRAM"), dynamic random-access memory ("DRAM"), and synchronous dynamic random-access memory ("SDRAM"). Other types of RAM also may be used to implement the system memory. The system memory 220 may be implemented using a single memory module or multiple memory modules. While the system memory is depicted as being part of the integrator/regulator 200, one skilled in the art will recognize that the system memory may be separate from the integrator/regulator without departing from the scope of the subject technology. It should also be appreciated that the system memory 220 may include, or operate in conjunction with, a non-volatile storage device such as the storage media 240.

The storage media 240 may include a hard disk, a compact disc, a digital versatile disc ("DVD"), a Blu-ray disc, a magnetic tape, a flash memory, other non-volatile memory device, a solid-state drive ("SSD"), any magnetic storage device, any optical storage device, any electrical storage device, any semiconductor storage device, any physical-based storage device, any other data storage device, or any combination or multiplicity thereof. The storage media 240 may store one or more operating systems, application programs and program modules such as a module, data, or any other information. The storage media 240 may be part of, or connected to, the integrator/regulator 200. The storage media may also be part of one or more other computing devices that are in communication with the integrator/regulator 200 such as one or more neural sensors, other computers, database servers, cloud storage, network attached storage, and so forth.

The modules 230 may comprise one or more hardware or software elements configured to facilitate the integrator/regulator 200 with performing the various methods and processing functions presented herein. The modules 230 may include one or more sequences of instructions stored as software or firmware in association with the system memory 220, the storage media 240, or both. The storage media 240 may therefore represent examples of machine- or computer-readable media on which instructions or code may be stored for execution by the processor. Machine- or computer-readable media may generally refer to any medium or media used to provide instructions to the processor. Such machine or computer-readable media associated with the modules may comprise a computer software product. It should be appreciated that a computer software product comprising the modules 230 may also be associated with one or more processes or methods for delivering the module to the integrator/regulator 200 via the network, any signal-bearing medium, or any other communication or delivery technology. The modules 230 may also comprise hardware circuits or information for configuring hardware circuits such as microcode or configuration information for an FPGA or other PLD.

The input/output ("I/O") interface 280 may be configured to couple to one or more external devices, to receive data from the one or more external devices, and to send data to the one or more external devices. Such external devices along with the various internal devices may also be known as peripheral devices. The I/O interface 280 may include both electrical and physical connections for operably coupling the various peripheral devices to the integrator/regulator 200 or the processor 210. The I/O interface 280 may be configured to communicate data, addresses, and control signals between the peripheral devices, the computing device, or the processor. The I/O interface 280 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attachment ("ATA"), serial ATA ("SATA"), universal serial bus ("USB"), Thunderbolt, FireWire, various video buses, and the like. The I/O interface may be configured to implement only one interface or bus technology. Alternatively, the I/O interface may be configured to implement multiple interfaces or bus technologies. The I/O interface may be configured as part of, all of, or to operate in conjunction with, the system bus 270. The I/O interface 280 may include one or more buffers for buffering transmissions between one or more external devices, internal devices, the computing device 200, or the processor 210.

In addition to the biomonitoring devices, neural sensors, input devices and output devices discussed above, the I/O interface 280 may couple the integrator/regulator 200 to various other peripherals. Exemplary input peripherals may include mice, touch-screens, scanners, biometric readers, electronic digitizers, sensors, receivers, touchpads, trackballs, cameras, microphones, keyboards, any other pointing devices, or any combinations thereof. Exemplary output peripherals may include projectors, cathode ray tube ("CRT") displays, liquid crystal displays ("LCD"), light-emitting diode ("LED") displays, organic light-emitting diode ("OLED"), speakers, printers, tactile-feedback devices, automation control, robotic components, actuators, motors, fans, solenoids, valves, pumps, transmitters, signal emitters, lights, and so forth.

The integrator/regulator 200 may operate in a networked environment using logical connections through the network interface 260 to one or more other systems or computing devices across the network 250. The network 250 may include WANs, LANs, intranets, the Internet, wireless access networks, wired networks, mobile networks, telephone networks, optical networks, or combinations thereof. The network 250 may be packet switched, circuit switched, of any topology, and may use any communication protocol. Communication links within the network 250 may involve various digital or an analog communication media such as fiber optic cables, free-space optics, waveguides, electrical conductors, wireless links, antennas, radio-frequency communications, and so forth.

The processor 210 may be connected to the other elements of the integrator/regulator 200 or the various peripherals discussed herein through the system bus 270. It should be appreciated that the system bus 270 may be within the processor, outside the processor, or both. According to some embodiments, any of the processor 210, the other elements of the integrator/regulator 200, or the various peripherals discussed herein may be integrated into a single device such as a system on chip ("SOC"), system on package ("SOP"), or ASIC device.

In one embodiment, the integrator/regulator 200 may engage in communication with a client device (e.g., a user device and/or provider device) via a web browser or similar client application running on the user device. For example, a client application running on the user device may make a request for a specific resource using HTTP/HTTPS and the computing device may respond with the content of that resource or an error message if unable to do so. The resource may be data or a file stored in a database. The computing device can receive content from a user, possibly using HTTP/HTTPS.

Generally, a client application may be adapted to present various user interfaces to users. Such user interfaces may be based on user information stored on the user device and/or received from the integrator/regulator 200. Accordingly, each client application may comprise HTML data, images, videos, icons, and/or executable code. The executable code may be composed in Java, JavaScript, ECMAScript, Python, Ruby or any other programming languages suitable for execution or for translation into an executable form.

In one embodiment, communication between a client application and a server application running on the integrator/regulator 200 may involve the use of a translation and/or serialization module. A serialization module can convert an object from an in-memory representation to a serialized representation suitable for transmission via HTTP or another transport mechanism. For example, the serialization module may convert data from a native Python, Ruby, or Java in-memory representation into a JSON string for communication over the client-to-server transport protocol. After the JSON string is received, a de-serialization module may convert the JSON string back into the native Python, Ruby, or Java in-memory representation for use by the client application or the server application.

It will be apparent to one of ordinary skill in the art that, in certain embodiments, any of the functionality of the integrator/regulator 200 may be incorporated into a client device, and vice versa. Likewise, any functionality of a client application may be incorporated into a browser-based client, and such embodiments are intended to be fully within the scope of this disclosure. For example, a browser-based client application could be configured for offline work by adding local storage capability, and a native application could be distributed for various native platforms via a software layer that executes the browser-based program on the native platform.

Methods

Figure 3:
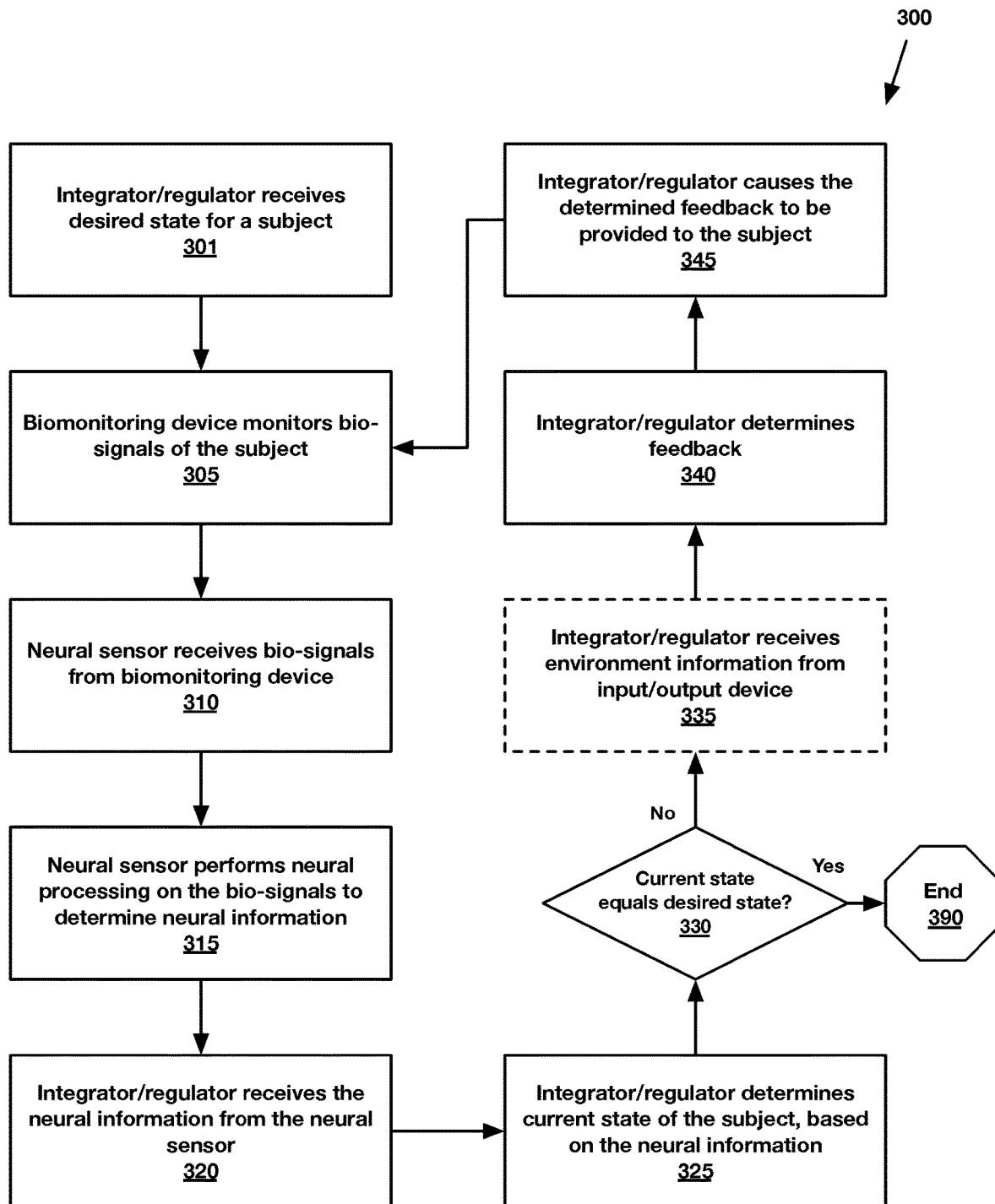
FIG. 3 shows an exemplary method 300 of monitoring bio-signals associated with a subject, determining neural information relating to the bio-signals, and providing feedback to the subject based on the neural information and/or a desired outcome.

Referring to FIG. 3, an exemplary method 300 of monitoring bio-signals associated with a subject, determining neural information relating to the bio-signals, and providing feedback to the subject based on the neural information, a state of the subject and/or a desired state is shown. The illustrated method 300 shows interactions that involve the responses of a subject, the sensing of these responses on a behavioral and physiological level, and the impact of these responses on feedback provided to the subject.

At step 301, an integrator/regulator receives or determines a desired state for a subject. In one embodiment, the desired state may be received from the subject (e.g., via a user device) or from another individual (e.g., via a provider device). Alternatively, the desired state may be determined by system based on a desired outcome, which itself may be received from the subject or another user and/or may be determined by the system. As discussed above, the system may determine a desired state that supports a specified outcome.

At step 305, the system monitors one or more structures of the subject in order to receive or determine bio-signals. Bio-signals may be monitored via any number of biomonitoring devices that comprise contact and/or noncontact sensors. And, at step 310, such bio-signals may be received, by one or more neural sensors, from the biomonitoring device(s).

At step 315, the neural sensors perform neural processing on the received bio-signals to determine neural information. As discussed above, the neural sensor is composed of hardware and software that applies extraction algorithms to extract neural information from bio-signals information. The neural sensors have the unique capacity to assess, in real time, the dynamic influence of brain and nervous system regulators on peripheral physiology. Thus, the extracted neural information may be more sensitive to mental, emotional, and physical processes than other techniques applied to monitor physiological state, including applications for vital signs monitoring and applications in closed-loop designs of medical devices.

Figure 4:
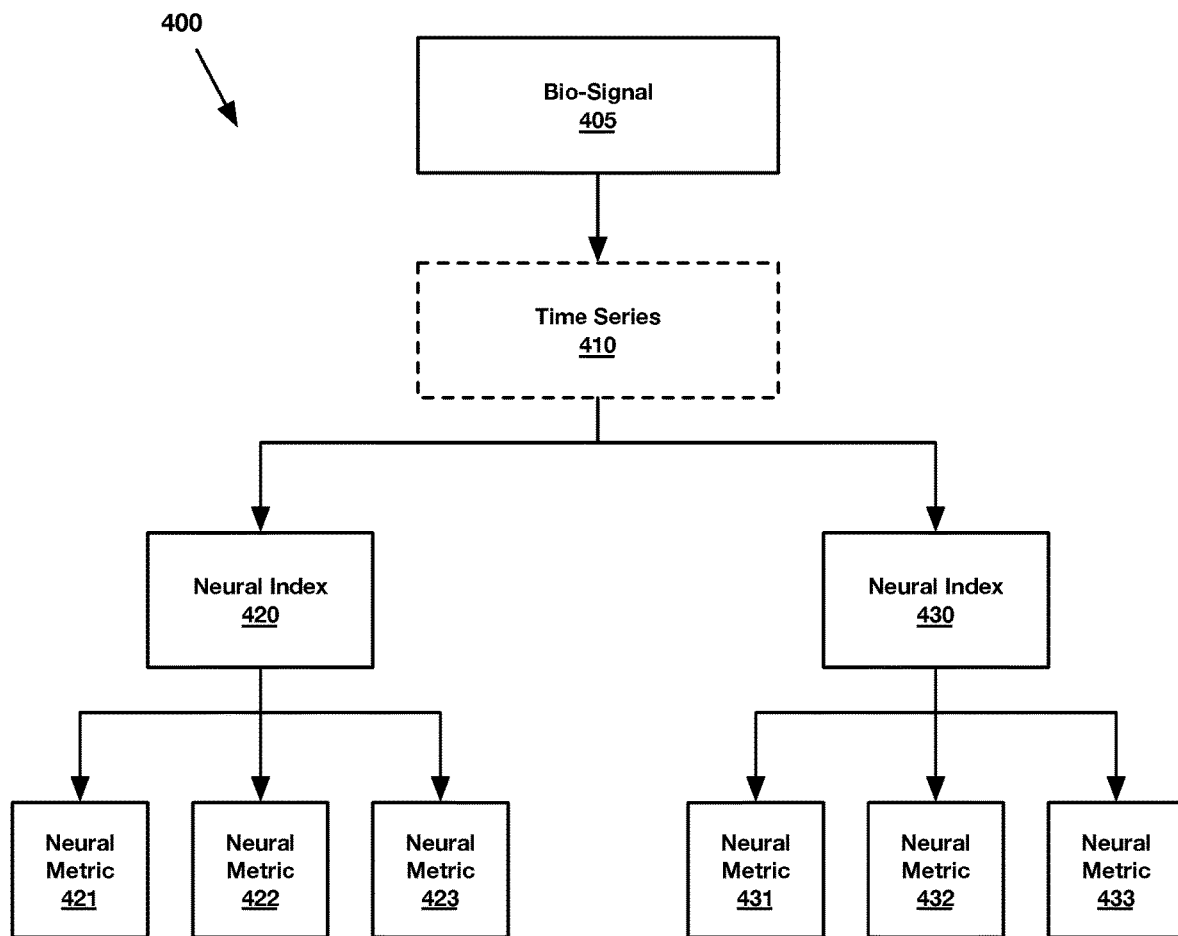
FIG. 4 shows an exemplary neural processing method 400 for determining neural information from a bio-signal.

An exemplary neural processing method 400 for determining neural information from a bio-signal is illustrated in FIG. 4. As shown, a bio-signal 405 received from the biomonitoring device represents a composite of underlying sources of variance (e.g., one or more neural indices, sensor noise, biological noise and/or measurement error). Generally, the sensory and motor pathways of the autonomic nervous system and endocrine system regulate visceral organs primarily through changes in pattern that are frequently reflected in the amplitude, slope, and period of oscillatory process.

In one embodiment, the neural sensors may pre-processes a bio-signal 405 to produce a time series (e.g., a time series of time intervals between sequential events) 410. In such embodiments, the neural sensors may employ pattern recognition algorithms to detect occurrences of events (e.g., an R-wave in an ECG) and/or peaks within events during a given time period. The neural sensor may then determine time intervals between sequential, detected events in order to produce an event intervals time series.

In certain embodiments, the neural sensor may employ error detection and correction algorithms to find and correct any erroneous intervals within a time series 410. For example, upon determining that a particular interval falls outside a predetermined range of acceptable interval times, the neural sensor may employ curve-fitting algorithms and/or integer arithmetic (e.g., dividing or adding intervals) to correct the data.

Next, the neural sensor performs neural signal processing on the time series 410. Specifically, the neural sensor performs a series of sequential signal processing operations including time sampling, detrending, filtering and/or curve fitting to extract separate, quantifiable neural indices (420, 430) from the time series 410. Each neural index (420, 430) may comprise a plurality of metrics that can be quantified over short time periods to produce a continuous and dynamically changing array of neural metrics (i.e., neural metric time series) (421-423, 431-433) relating to one or more of: amplitude, level, phase, slope, and/or time period (i.e., frequency). The duration of the time window in which the neural metrics are quantified ranges from a few seconds to minutes, hours or days. With short duration time windows, dynamic changes in each of the neural metrics can be monitored and other variables defined by algorithms applied to quantify the interactions among these neural metrics.

In certain embodiments, the neural sensor may employ the pattern of the neural metrics across time as another level of quantification. The patterns can be described, similar to component neural metrics, in terms of amplitude, phase, and period. In addition, the covariation among neural metrics including phase, slope, and coupling (e.g., coherence) may provide an additional level of metrics.

Returning to FIG. 3, at step 320, the neural sensors transmit the extracted neural information (e.g., neural indices and/or neural metrics) to an integrator/regulator, which may then determine a current state of the subject at step 325. In one embodiment, the integrator/regulator employs concepts from the Polyvagal Theory to determine a subject's state from the neural information received from the neural sensors and, optionally, any bio-signals received from the biomonitoring devices. The Polyvagal Theory is described in detail in the following references, each of which is incorporated by reference herein in its entirety: Porges, S. W., "Orienting in a defensive world: Mammalian modifications of our evolutionary heritage. A polyvagal theory," 1995, Psychophysiology, 32(4), 301-318; Porges, S. W., "The polyvagal perspective," Biological Psychology, 2007, 74(2), 116-143; Porges S. W., "The Polyvagal Theory: Neurophysiological Foundations of Emotions, Attachment, Communication, and Self-regulation," 2011, New York: WW Norton; and Porges S. W., "The Pocket Guide to The Polyvagal Theory: The Transformative Power of Feeling Safe," 2017, New York: WW Norton.

At step 330, the integrator/regulator determines whether the subject's current state is equal to the desired state. For example, the integrator/regulator may determine whether the neural information is within an acceptable range of neural information associated with the desired state. If the current state is equal to the desired state, the process may end 390. Otherwise, the process may continue to step 335.

At optional step 335, the integrator/regulator may receive environment information from one or more input devices located within the subject's environment. Such environment information may relate to the various acoustic stimuli, visual stimuli, tactile stimuli and/or olfactory stimuli present within the environment.

At step 340, the integrator/regulator may determine feedback comprising specific stimuli to be provided to the subject and/or modifications to be made to environmental stimuli. And, at step 345, the integrator/regulator provides the determined feedback to the subject.

The feedback may be provided to the subject directly by the integrator/regulator and/or indirectly via a user device or separate output device. As discussed above, the output device/user device may be in direct communication with the integrator/regulator and/or may be in indirect communication with the integrator/regulator (e.g., via a network).

Generally, the integrator/regulator leverages knowledge of neurophysiological regulation of structures to determine appropriate feedback to be provided to the subject. To that end, the integrator/regulator may employ the neural information, the current state, the desired state and, optionally, the environment information to determine appropriate feedback that will trigger specific sensory receptors (e.g., sensory pathways that function as efficient neural portals), such that the subject's autonomic nervous system and/or endocrine system may be regulated to modify the subject's current state to a desired state. It will be appreciated that both the autonomic nervous system and the endocrine system are feedback systems with continuous input from visceral organs, and the integrator/regulator may, in addition to determining appropriate feedback, select a structure (i.e., a target structure) to which receive any determined feedback may be directed.

In one embodiment, the feedback may be presented to the subject as discrete stimuli. Exemplary discrete stimuli may include, but are not limited to: administering a medication or other substance, displaying an image or video to a subject, transmitting a notification to the subject, changing an output volume of a user device, changing display characteristics of a user device (e.g., color profile, brightness, contrast, etc.), causing a user device to vibrate, providing electrical stimulation to the subject, and/or other direct interventions into a target structure.

In another embodiment, the feedback may additionally or alternatively be presented to the subject as one or more modifications of environmental stimuli (i.e., background and/or contextual stimuli present in the subject's environment). For example, the system may increase/decrease volume of background sounds; filter, mask, or selectively cancel background sounds; modify intonation of real or synthesized voices within the environment; cause music to start or stop playing; turn on/off display devices; cause images and/or videos to start or stop playing on one or more display devices; modify properties of images and/or videos playing on one or more display devices (e.g., playback speed, framerate, color profile, brightness, etc.); increase/decrease brightness of one or more lights in the environment; modify color of one or more lights; turn on/off one or more lights; increase/decrease temperature (e.g., via control one or more fans, heaters, cooling units in the environment); modify pattern or gradient of ambient temperature; turn on/off vibration motors in the environment; and/or modify pattern and/or intensity of vibrations output via vibration motors.

In embodiments where feedback is presented as modifications to environmental stimuli, the integrator/regulator may employ "neuroception" to manipulate the subject's state without their awareness. As explained by the Polyvagal Theory, neuroception is a nonconscious, neural process that evaluates risk in the environment by detecting signals of safety, danger, and threats to life. Such signals—usually through auditory and visual sensory channels—rapidly change physiological state to promote survival. These concepts are described in detail in, for example, Porges, S. W., "Social Engagement and Attachment: A Phylogenetic Perspective," Annals of the New York Academy of Sciences, 2003, pp. 31-47, 1008 (incorporated herein by reference in its entirety).

Functionally, a neuroception of safety promotes a calm biobehavioral state regulated by an integrated social engagement system. The integrated social engagement system includes the nerves that are involved in regulating the muscles of the face, which enable positive facial expressions; the muscles of the middle ear that optimize the listening to human voice; the muscles of the larynx and pharynx that enable comforting vocalizations to be projected; and the myelinated vagal pathways originated in nucleus ambiguus that calm (slow) the heart and dampen sympathetic activity (e.g., fight/flight behaviors).

In contrast, signals of danger promote a rapid and graded functional withdrawal of the myelinated vagal system and a dampening of the neural tone to the social engagement system (e.g., loss of facial muscle tone, intonation of voice, and an inability to listen) allowing for the evolutionarily older survival-based systems to activate in order to meet environmental challenges. In the case of such challenges, state regulation follows the well-documented principles of Jacksonian dissolution (1884), with phylogenetically older, survival-oriented systems becoming recruited when more-recent evolutionarily circuits fail to enable the organism to navigate to safety. Consistent with dissolution, the Polyvagal Theory proposes that withdrawal of the social engagement system enables mobilization reactions. Mobilization reactions are often associated with fight/flight behaviors, which are facilitated by the sympathetic nervous system.

According to Polyvagal Theory, there is a second defense system that may trigger when mobilization is not adaptive in the context of the specific threat. This frequently occurs in life-threatening situations that do not allow for fight or flight behaviors. Under these situations an evolutionarily ancient defense system may be elicited. This system is characterized by behavioral immobilization, such as death feigning and vasovagal syncope (fainting) during which there are drops in blood pressure and heart rate. The neural mechanisms regulating this response pattern reflect an evolutionarily ancient circuit in the brainstem, the unmyelinated dorsal vagal complex, which regulates the unmyelinated vagal pathways and is shared among most vertebrates.

In one particular embodiment where acoustic stimuli are provided to the subject (e.g., via discreet feedback and/or neuroception), the acoustic stimuli may comprise human speech, human singing, instrumental music, synthesized music and combinations thereof may. For example, the acoustic stimuli may have acoustic properties similar to a mother singing a lullaby to infant. Prerecorded vocal or instrumental music may be selected based on a number of variables, such as but not limited to: frequency band, modulation of intonation within the frequency band, tempo, volume and/or modulation of volume. The frequency characteristics of the acoustic stimuli may be selected to emphasize the frequency band in which information related to human speech is conveyed, consistent and overlapping with the documented frequency band and weights associated with the Index of Articulation ("AI") as defined in American National Standard ANSI S3.5-1997 American National Standard ANSI S3.5-1997 ("Methods for Calculation of the Speech Intelligibility Index") and/or the Speech Intelligibility Index ("RI") as described in Pavlovic, C. V. "Derivation of primary parameters and procedure's for use in speech intelligibility predictions," J. Acoust. Soc. Am. 82 (1987): 413-422 (each of which is incorporated by reference herein in its entirety). The AI is a quantified expression of the proportion of the average speech signal that is audible to a person in a given environment and is expressed on a scale of 0 to 1.0, with 1.0 representing perfect audible speech. The SII quantifies the intelligibility of speech and it is also expressed on a scale of 0 to 1.0. An acoustic input signal may be processed by an audio processing device such that acoustic stimuli is produced and eventually transmitted to the subject. Generally, the acoustic stimuli signal may be designed to exercise the neural regulation of the middle-ear structures and muscles of the subject.

It will be appreciated that, as the subject's physiology changes in response to the provided feedback, neural information may be continually extracted from bio-signals. The neural information may be continuously conveyed to the integrator/regulator such that it may dynamically generate and provide appropriate feedback to the subject. That is, the system continuously monitors the physiology of the subject, interprets the subject's current state, and dynamically determines which features of the feedback stimuli should be changed in order to assist the subject in achieving a desired state.

Figure 5:
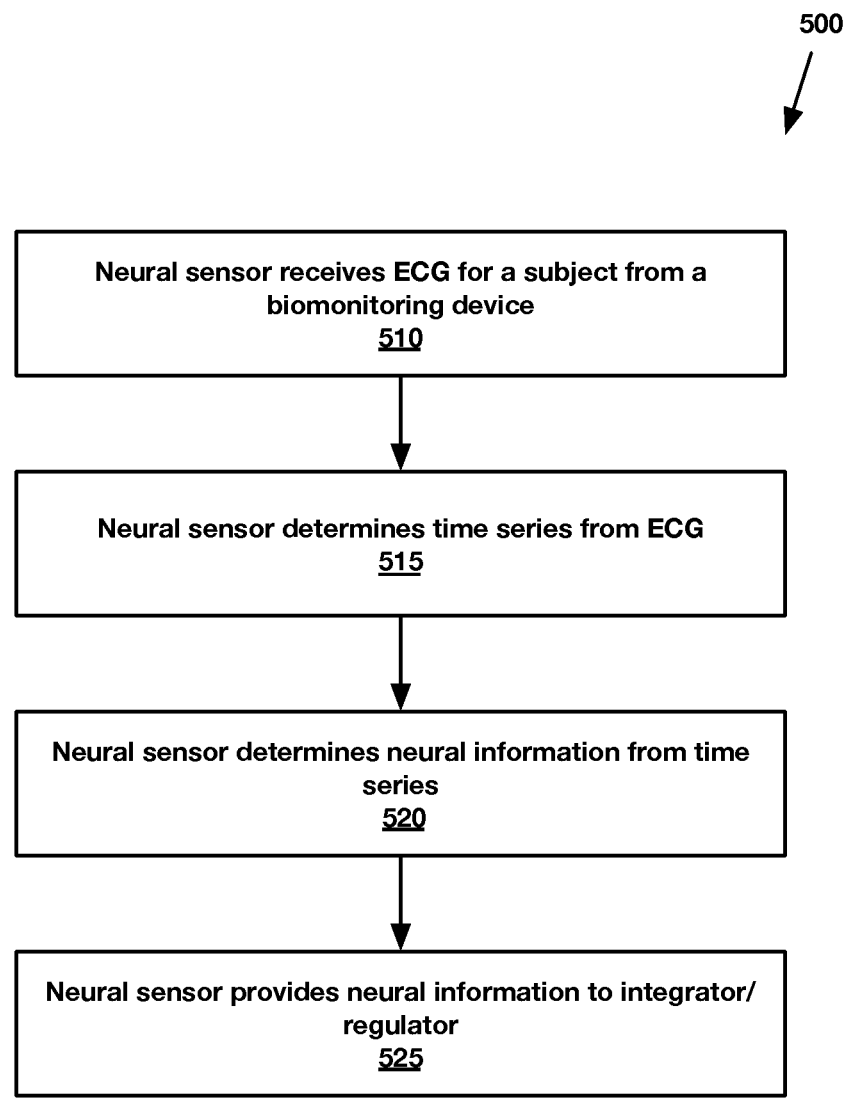
FIG. 5 shows an exemplary neural processing method 500 of determining neural information from an electrocardiogram ("ECG").

Referring to FIG. 5, an exemplary neural processing method 500 of determining neural information from an ECG is illustrated. Generally, an ECG bio-signal may be monitored by applying a physical sensor comprising at least two electrodes across the frontal plane of a subject's heart. ECG may be assessed with, for example, a BIOPAC MP150 physiological acquisition system (Biopac Systems, Inc., Santa Barbara, Calif.), an EZ-IBI interbeat interval monitor (UFI, Morro Bay, Calif.), and/or a BIOLOG ambulatory heart rate monitor (UFI, Morro Bay, Calif.).

With appropriate leads and placement of the electrodes, the ECG provides detailed information about the electrical activity of the subject's heart and tracks the depolarization and repolarization of the atria and ventricles as the heart beats. The ECG thus includes an accurate index of the timing of the initiation of sequential heartbeats to provide an accurate and sensitive time series of beat-to-beat heart rate or heart period (i.e., the time intervals between sequential heart beats).

At step 510, the neural sensor receives the ECG bio-signal from a biomonitoring device. And at step 515, the neural sensor pre-processes the ECG to produce a time series of interbeat intervals ("IBIs") or heart periods.

In one specific embodiment, the neural sensor may employ event/peak detection to determine occurrences of R-waves in the ECG. For example, a pattern recognition algorithm may be employed to detect occurrences of R-wave peaks during a given time period, with an accuracy of about 1 ms. The neural sensor may then extract the times between sequential R-wave peaks over a given time period to produce a time series of IBIs. In one embodiment, the neural sensor may utilize a time period of about 500 ms or less.

In certain embodiments, the neural sensor may employ error detection and correction algorithms to find and correct any erroneous IBIs within the time series. For example, upon determining that a particular IBI falls outside a predetermined range of acceptable interval times, the neural sensor may employ integer arithmetic (e.g., dividing or adding IBIs) to correct the data.

At step 520, the neural sensor performs neural signal processing on the IBI time series. Specifically, the neural sensor performs a series of sequential signal processing operations including time sampling, detrending, filtering and/or curve fitting to extract neural information. Such neural information may comprise component signals representing component heart rate patterns due to different neural influences.

Embedded in the IBI time series are well-documented and validated neural influences. Direct influences through myelinated vagal pathways on the sinoatrial node are manifest as respiratory pattern in the IBI time series. And low-frequency heart rate variability ("LF-HRV") oscillations, which are slower than spontaneous breathing, occur at a lower frequency due to baroreceptor feedback through vagal pathways.

Figure 6:
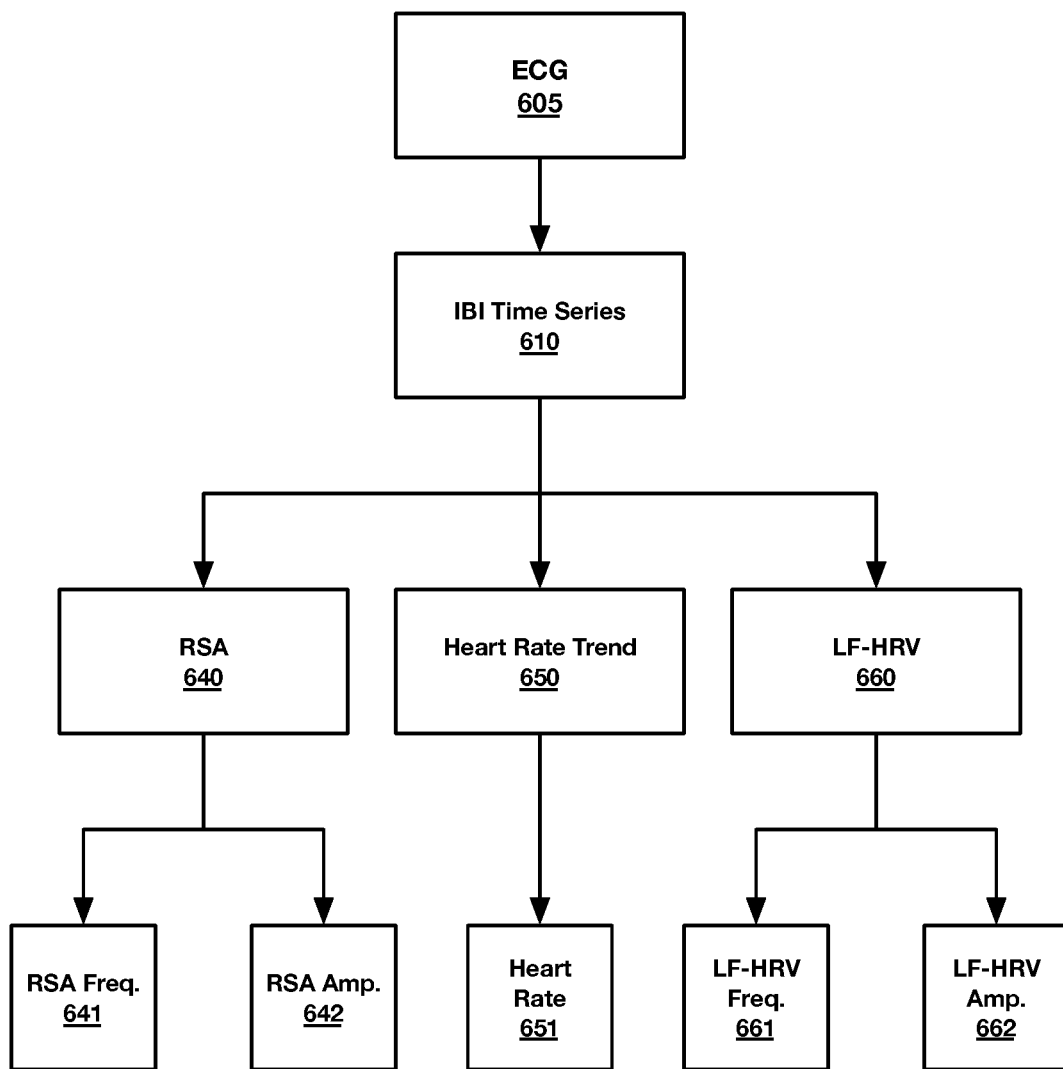
FIG. 6 shows exemplary neural information determined from an ECG.

Accordingly, as shown in FIG. 6, a neural sensor may extract some or all of the following neural indices embedded within an IBI time series 610 associated with an ECG 605:

(1) the slow moving trend in heart rate upon which respiratory sinus arrhythmia ("RSA") and LF-HRV are superimposed 650; (2) RSA 640, the oscillations associated with spontaneous respiration mediated via myelinated vagal pathways; and/or (3) LF-HRV, the slow oscillations in heart rate associated with baroreceptor regulation and vasomotor feedback 660.

The neural sensor may further quantify each of the neural indices (640, 650, 660) to an array of neural metrics (641, 642, 651, 661, 662). For example, the heart rate trend neural index 650 may be quantified as heart rate 651; the RSA neural index 640 may be quantified to RSA frequency 641 (an accurate index of respiration rate) and RSA amplitude 642 (an index of cardiac vagal tone); and the LF-HRV neural index 660 may be quantified to LF-HRV frequency 661 (an accurate index of feedback on the heart due to blood pressure and vasomotor activity) and LF-HRV amplitude 662 (an index of vagal mechanisms including influences from dorsal and ventral vagal nuclei).

As a specific example, RSA amplitude 642 may be quantified via the method described in U.S. Pat. No. 4,510,944 to Porges (incorporated by reference herein in its entirety). Specifically, (1) the IBI time series 610 may be filtered to create a smoothed template (e.g., via a moving polynomial filter), (2) the template may be subtracted from the original IBI time series to generate a detrended residual series, (3) the detrended time series may be bandpassed to extract variance in the heart period pattern associated with spontaneous breathing, and (4) the natural logarithm of the variance of the bandpassed time series may be calculated as the measure of the amplitude of RSA 642.

The duration of the time window in which each of the neural metrics (641, 642, 651, 661, 662) is quantified ranges from a few seconds to a few minutes, hours or days. With short-duration time windows, dynamic changes in each of the neural metrics can be monitored and other variables defined by algorithms applied to quantify the interactions among these neural metrics. For example, a measure of "vagal efficiency" in regulating heart rate can be calculated by time domain regression analyses or frequency domain coherence analyses that would define metrics describing the coupling between heart rate 651 and RSA amplitude 642. In this example, "vagal efficiency" would be defined as greater when the two variables are more tightly coupled, which implies that the transitory changes in heart rate 651 co-occur with synchronous changes in RSA amplitude 642 (a validated index of vagal regulation of the heart).

It will be appreciated that the neural sensor does not focus on quantifying the variations in the shape of the ECG 605 that indicate arrhythmias and other anomalies monitored by cardiologists as indices of health and disease. Rather, the neural sensor extracts neural indices (640, 650, 660), which relate to specific neural influences mediated by the autonomic nervous system and manifested on the heart through variations in beat-to-beat heart rate. These neural influences are reflected as the temporal pattern of beat-to-beat heart rate changes. Specific identifying neural influences on the heart are conveyed through neural pathways associated with the autonomic nervous system. The origin of the major neural input from the parasympathetic component of the autonomic nervous system is transmitted from the brainstem, through the vagus (cranial nerve X), to the sino-atrial node—the heart's pacemaker. Vagal pathways produce a pattern of inhibition on the heart's pacemaker and impose a rhythmic slowing and cessation of slowing heart rate. In contrast, nerves from the sympathetic nervous system increase the rate the heart beats with a less well-defined (if any) rhythmicity. The neural influences on the heart, through both branches of the autonomic nervous system, are manifest in both the level of heart rate and the beat-to-beat variations in heart rate, which is also known as heart rate variability ("HRV").

Returning to FIG. 5, the method continues at step 525, where an integrator/regulator receives the neural information from the neural sensor. As discussed above, the integrator/regulator may determine appropriate feedback to be provided to the subject, based on the neural information (e.g., neural indices and neural metrics), a current state of the subject and a desired state. And the determined feedback may be provided to the subject either directly by the integrator/regulator or indirectly via an output device in communication with the integrator/regulator. It will be appreciated that the method 500 may be repeated as desired or required (e.g., a predetermined number of times, a predetermined time period, until a desired state is achieved, until a desired outcome is achieved and/or until the current state is materially changed).

Figure 7:
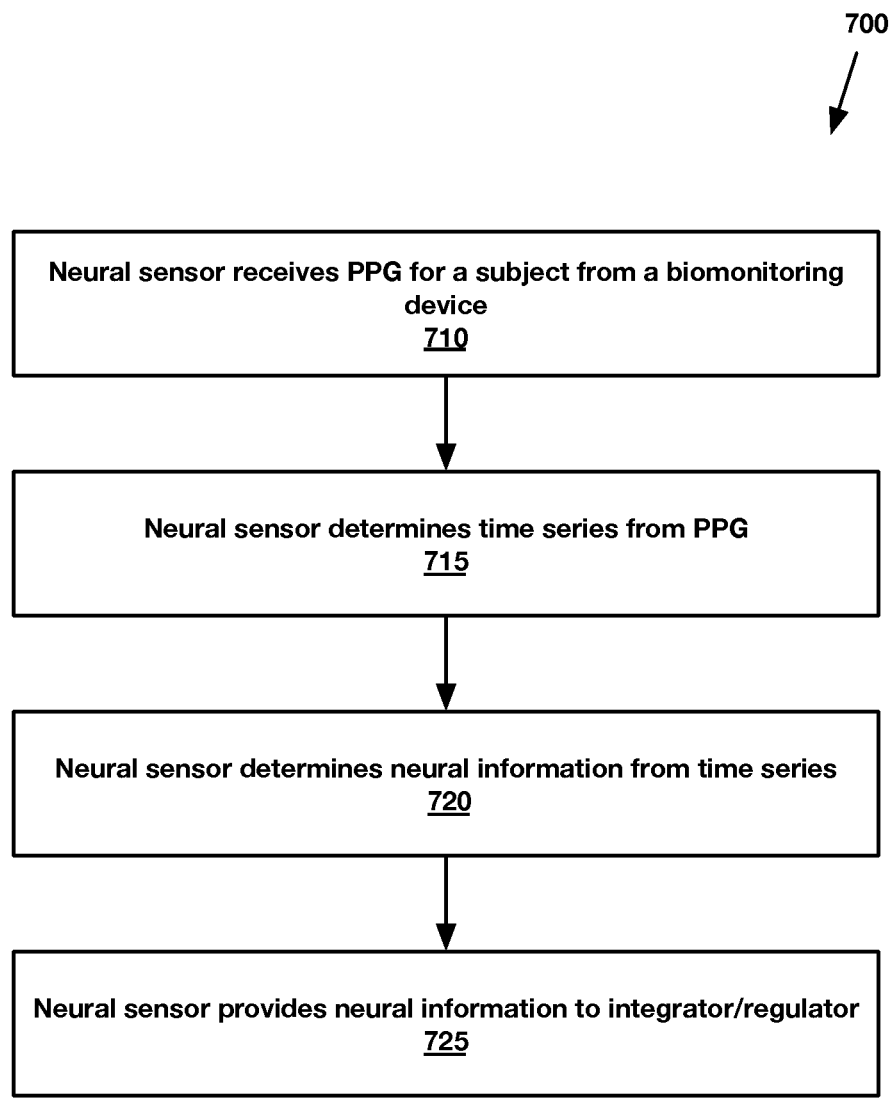
FIG. 7 shows an exemplary neural processing method 700 of determining neural information from a photoplethysmograph ("PPG").

Referring to FIG. 7, an exemplary neural processing method 700 of determining neural information from a PPG is illustrated. Generally, a PPG may be monitored by a photosensor to detect dynamic changes in light absorption and reflection from the skin of a subject. In one embodiment, the PPG may be monitored by a biomonitoring device comprising a contact sensor, such as an earlobe PPG. For example, a contact PPG may be assessed with a BIOPAC MP150 physiological acquisition system (Biopac Systems, Inc., Santa Barbara, Calif.).

In another embodiment, the PPG may be monitored by a biomonitoring device comprising a noncontact photosensor placed at a distance from the subject. For example, a noncontact PPG may be assessed with any of the systems described in the following references, each of which is incorporated by reference herein it its entirety: U.S. Pat. No. 10,004,410 to Porges et al.; Davila, M. I. et al., "The physiocam: Cardiac pulse, continuously monitored by a color video camera," 2016, Journal of Medical Devices, 10(2), 020951; and Davila, M. I., et al., "The Physiocam: a novel non-contact sensor to measure heart rate variability in clinical and field applications," 2017, Frontiers in Public Health, 5.

Whether obtained via a contact sensor or a noncontact sensor, the PPG provides a digital representation of the subject's arterial pulse signal through signal processing. When light travels through biological tissues, it is absorbed by bones, skin pigments, and both venous and arterial blood. Because light is more strongly absorbed by blood than the surrounding tissues, the changes in blood flow can be detected by the PPG as changes in the intensity of light being reflected from the skin.

A PPG can be designed to output an electrical signal in which the voltage level is related to the quantity of blood flowing through the blood vessels producing an analog representation of continuous pulse wave activity superimposed on slower vasomotor activity characterized by oscillations and aperiodic trends. As the heart beats, the pulse wave is propagated through the vascular system and dynamically changes blood flow in the area of skin being monitored by the PPG. This enables the PPG to provide information relating to the timing of sequential heartbeats (similar to an ECG).

At step 710, the neural sensor receives the PPG bio-signal from a biomonitoring device. And at step 715, the neural sensor pre-processes the PPG to determine a pulse wave time series (i.e., a time series of time intervals between sequential pulse waves). As discussed above, pre-processing may include event/peak detection and/or error detection/correction.

At step 720, the neural sensor performs neural signal processing on the pulse wave time series. Specifically, the neural sensor performs a series of sequential signal processing operations including time sampling, detrending, filtering and/or curve fitting to extract component signals including various neural influences.

In addition to the modulation of beat-to-beat heart rate that provides robust information related to vagal (parasympathetic) influences on the heart, the PPG is also capable of indexing the influence of the sympathetic nervous system on vascular tone reflected in the amplitude and slope of the pulse wave and at frequencies slower than heart rate reflecting dynamic changes in vascular tone (i.e., vasomotor tone).

The sympathetic influences on vascular tone are also influenced by breathing. For example, synchronous with breathing there are systematic changes in the amplitude of the pulse wave pattern and vascular tone. Quantification of these synchronous changes can be used to monitor respiration rate.

Figure 8:
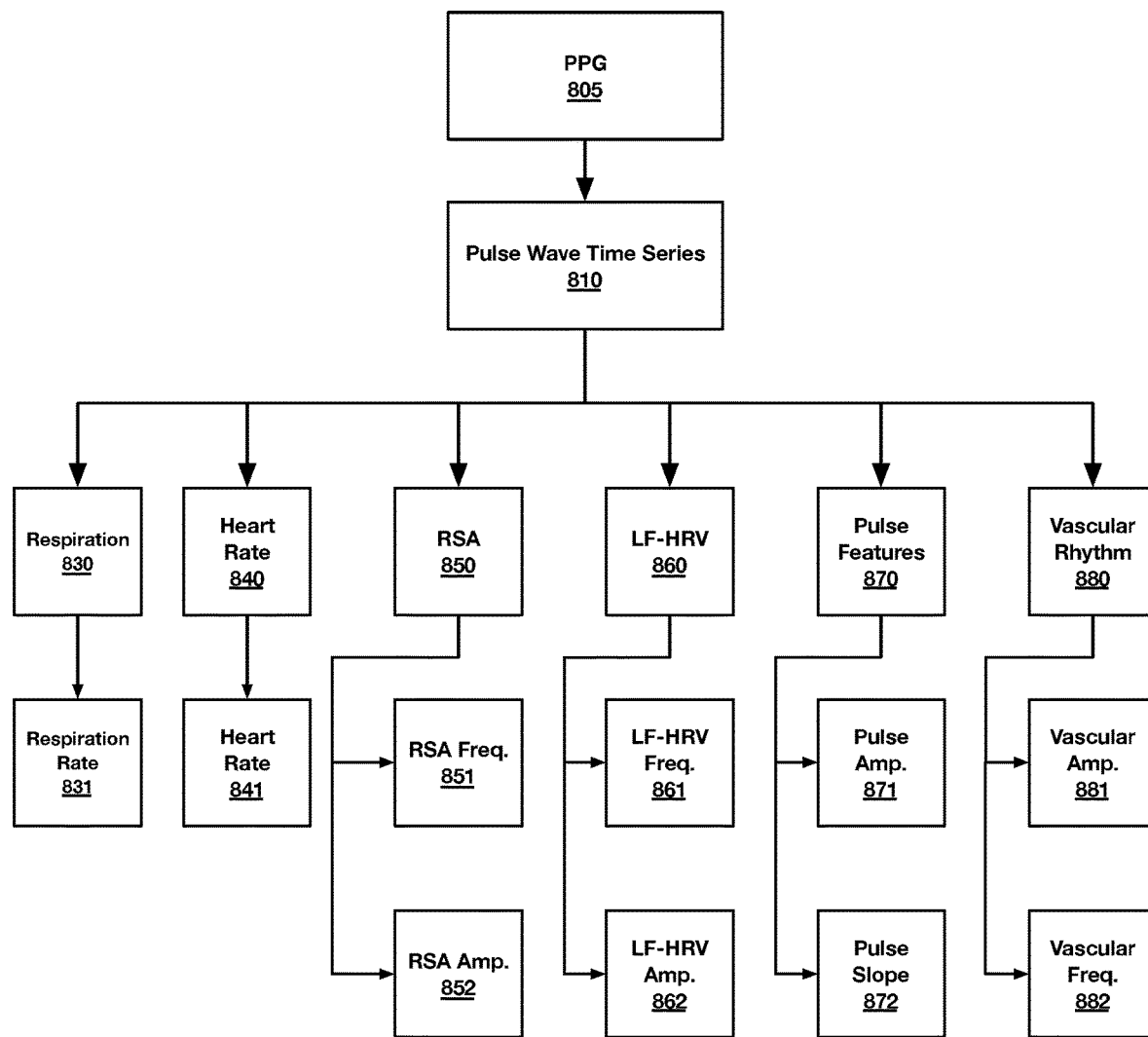
FIG. 8 shows exemplary neural information determined from a PPG.

As shown in FIG. 8, the neural sensor may extract neural indices embedded within the pulse wave time series 810 of a PPG 805, including: respiration 830, heart rate 840, RSA 850, LF-HRV 860, pulse features 870 and vascular rhythm 880. The neural sensor may further quantify each of the neural indices (830, 840, 850, 860, 870) to an array of neural metrics (831, 841, 851, 852, 861, 862, 871, 872, 881, 882). For example, the respiration neural index 830 may be quantified as respiration rate 831; the heart rate trend neural index 840 may be quantified as heart rate 841; the RSA neural index 850 may be quantified to RSA frequency 851 and RSA amplitude 852; the LF-HRV neural index 860 may be quantified to LF-HRV frequency 861 and LF-HRV amplitude 862; the pulse features neural index 870 may be quantified to pulse amplitude 871 and pulse slope 872; and the vascular rhythm neural index 880 may be quantified to vascular frequency 881 and vascular amplitude 882.

Returning to FIG. 7, the method continues at step 725, where an integrator/regulator receives the neural information (e.g., neural indices and/or neural metrics) from the neural sensor. As discussed above, the integrator/regulator may determine appropriate feedback to be provided to the subject, based on the neural information, a current state of the subject and a desired state. And the determined feedback may be provided to the subject either directly by the integrator/regulator or indirectly via an output device in communication with the integrator/regulator. It will be appreciated that the method 700 may be repeated as desired or required (e.g., a predetermined number of times, a predetermined time period, until a desired state is achieved, until a desired outcome is achieved and/or until the current state is materially changed).

It will be appreciated that, although particular sets of neural metrics are described above, additional or alternative neural metrics may be determined via neural signal processing. Moreover, it will be appreciated that the determined neural metrics and/or sequence of processes will depend on the bio-signal(s) being monitored and may be the same or different for different monitored bio-signal(s).

Various embodiments are described in this specification, with reference to the detailed discussed above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein, and the corresponding drawings, are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those skilled in the art, and such modifications are also intended to fall within the scope of the appended claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

All references including patents, patent applications and publications cited herein are incorporated herein by reference in their entirety and for all purposes to the same extent as if each individual publication or patent or patent application was specifically and individually indicated to be incorporated by reference in its entirety for all purposes.

What is claimed is:
1. A method comprising:
   A. receiving bio-signal information relating to bio-signals associated with a monitored physiological structure of a subject;
   B. determining neural information from the bio-signal information, the neural information comprising:
      one or more neural indices determined from the bio-signal information; and
      one or more neural metrics determined from at least one neural index of the one or more neural indices;

C. determining a current state of the subject based on the neural information;
D. upon determining that the current state is different than a desired state:
   determining feedback to be provided to the subject, based on the current state and the desired state; and
   providing the determined feedback to the subject to thereby modify neural regulation of the monitored physiological structure of the subject; and
E. repeating steps A-D until the current state is substantially similar to the desired state or a predetermined time period expires.

2. A method according to claim 1, wherein the bio-signals are selected from the group consisting of: heart rate, pulse rate, respiratory rate, blood pressure, cardiac rhythm, oxygen saturation, pH, pulse wave slope, pulse wave amplitude, vascular tone, an electromagnetic field, sudomotor activity, an electrocardiogram ("ECG"), an electrogastrogram ("EGG"), an electroencephalogram ("EEGs"), an electromyogram ("EMG"), an electrooculography ("EOG"), electrodermal activity ("EDA"), galvanic skin response ("GSR"), electrical potential of a body surface, electrical resistance of a body surface, a mechanomyogram ("MMG"), an endocrine level, an immune reaction, cerebral spinal fluid pressure, pupil diameter, vocalization, movement, body temperature, and blood glucose level.

3. A method according to claim 2, wherein the bio-signals comprise a vocalization.

4. A method according to claim 3, wherein the one or more neural indices comprises one or more of: frequency band of the vocalization, modulation of intonation within the frequency band, tempo of the vocalization, volume of the vocalization, and modulation of the volume.

5. A method according to claim 1, wherein the desired state relates to a physiological, emotional or behavioral state.

6. A method according to claim 1, wherein the desired state differentially and selectively supports a desired outcome relating to the subject, the desired outcome selected from the group consisting of: increasing attentiveness, improving cognitive ability, improving concentration, improving critical thinking, improving creativity, improving productivity, improving health, promoting growth, increasing restoration, improving recovery following illness or injury, increasing mobility, decreasing mobility, improving performance of a physical activity, improving ability to engage in spontaneous interactions with others, increasing sexual desire, improving sexual function, improving ability to eat or drink, improving digestion, improving gastrointestinal motility, increasing pleasure relating to ingestion of a food or a drink, improving ability to sing, reducing one or more medically unexplained symptoms relating to an autonomic state, improving quality of vocalizations, improving function of a visceral organ, increasing relaxation, improving ability to mediate, improving sleep quality, and improving ability to wake from sleep.

7. A method according to claim 6, wherein:
the desired state is characterized by a decreased vagal influence on a heart of the subject; and
the desired outcome comprises one or more of: increasing mobility, improving concentration, improving attentiveness, improving performance of a physical activity.

8. A method according to claim 6, wherein:
the desired state is characterized by an increased vagal influence on a heart of the subject; and
the desired outcome comprises one or more of: decreasing mobility and improving ability to engage in spontaneous interactions with others.

9. A method according to claim 6, wherein:
the desired outcome is received from a user; and
the desired state is determined based on the desired outcome.

10. A method according to claim 1, wherein the one or more neural indices are determined from a time series relating to the bio-signal information.

11. A method according to claim 10, further comprising:
determining an error in the time series; and
correcting the error via application of a curve-fitting algorithm.

12. A method according to claim 1, wherein the one or more neural indices are manifested in the bio-signal information as levels, trends, periodicities and/or quasi-periodicities.

13. A method according to claim 1, wherein each of the neural indices relates to neural regulation, via an identifiable neural pathway, of the monitored physiological structure.

14. A method according to claim 1, wherein each of the one or more neural metrics relates to a property of the at least one neural index, the property selected from the group consisting of: amplitude, level, phase, slope and frequency.

15. A method according to claim 14, wherein each of the one or more neural metrics comprises a time series associated with a plurality of time periods during which the property is quantified.

16. A method according to claim 15, further comprising:
determining one or more patterns relating to at least one of the neural metrics time series,
wherein the neural information further comprises the one or more patterns.

17. A method according to claim 15, further comprising:
determining one or more covariations among the neural metrics,
wherein the neural information further comprises the one or more covariations.

18. A method according to claim 17, wherein each of the one or more covariations relates to phase, slope or coupling.

19. A method according to claim 1, wherein the feedback comprises one or more of: acoustic stimuli, visual stimuli, tactile stimuli and/or olfactory stimuli.

20. A method according to claim 19, wherein the feedback comprises acoustic stimuli selected from the group consisting of human speech, human singing, instrumental music and synthesized music.

21. A method according to claim 20, wherein the feedback further comprises visual stimuli synchronized to the acoustic stimuli.

22. A method according to claim 1, further comprising:
receiving environment information relating to environmental stimuli present within an environment of the subject,
wherein said determining the feedback is further based on the environment information.

23. A method according to claim 22, wherein:
the determined feedback is provided to the subject via modification of the environmental stimuli; and
said modifying neural regulation of the monitored physiological structure of the subject occurs without awareness of the subject.

24. A method according to claim 1, wherein the neural information comprises a measure of vagal efficiency in regulating heart rate determined from the one or more neural metrics.

25. A method according to claim 1, wherein the one or more neural indices does not comprise respiratory sinus arrhythmia ("RSA").

26. A method comprising:
receiving, by a neural sensor, from a biomonitoring device, bio-signal information relating to bio-signals associated with a monitored physiological structure of a subject;
extracting, by the neural sensor, one or more neural indices from the bio-signal information,
wherein each of the one or more neural indices relates to neural regulation, via an identifiable neural pathway, of the monitored physiological structure; and
determining, by the neural sensor, one or more neural metrics from at least one neural index of the one or more neural indices,
wherein each of the one or more neural metrics relates to a property of the at least one neural index selected from the group consisting of: amplitude, level, phase, slope and frequency; and
transmitting, by the neural sensor, to an integrator/regulator, neural information comprising the one or more neural indices and the one or more neural metrics.

27. A method according to claim 26, wherein each of the one or more neural metrics comprises a time series associated with a plurality of time periods during which the property is quantified.

28. A method according to claim 27, further comprising:
determining, by the neural sensor, one or more patterns relating to at least one of the neural metrics time series,
wherein the neural information further comprises the one or more patterns.

29. A method according to claim 27, further comprising:
determining, by the neural sensor, one or more covariations among the neural metrics,
wherein the neural information further comprises the one or more covariations.

30. A method according to claim 29, wherein each of the one or more covariations relates to phase, slope or coupling.

31. A method according to claim 26, wherein:
the bio-signal information comprises an electrocardiogram ("ECG");
the one or more neural indices comprise one or more of: heart rate trend, respiratory sinus arrhythmia ("RSA"), and low-frequency heart rate variability ("LF-HRV"); and
the one or more neural metrics comprise one or more of: heart rate, RSA frequency, RSA amplitude, LF-HRV frequency, and LF-HRV amplitude.

32. A method according to claim 26, wherein:
the bio-signal information comprises a photoplethysmograph ("PPG");
the one or more neural indices comprise one or more of: respiration, heart rate, RSA, LF-HRV, pulse features and vascular rhythm; and
the one or more neural metrics comprise one or more of: respiration rate, heart rate, RSA frequency, RSA amplitude, LF-HRV frequency, LF-HRV amplitude, pulse amplitude, pulse slope, vascular frequency and vascular amplitude.

33. A method according to claim 26, wherein the bio-signals comprise a vocalization.

34. A method according to claim 33, wherein the one or more neural indices comprises one or more of: frequency band of the vocalization, modulation of intonation within the frequency band, tempo of the vocalization, volume of the vocalization, and modulation of the volume.

35. A method according to claim 26, further comprising:
determining, from the one or more neural metrics, a measure of vagal efficiency in regulating heart rate; and
transmitting, by the neural sensor, to the integrator/regulator, the measure of vagal efficiency.

36. A method according to claim 26, wherein the one or more neural indices does not comprise respiratory sinus arrhythmia ("RSA").

37. A method according to claim 26, wherein at least one of the one or more neural indices relates to neural regulation of a heart of the subject via a myelinated vagal pathway.

* * * * *